United States Patent
Palczewski et al.

(10) Patent No.: US 11,253,489 B2
(45) Date of Patent: Feb. 22, 2022

(54) VISUAL CYCLE MODULATORS

(71) Applicant: CASE WESTERN RESERVE UNIVERSITY, Cleveland, OH (US)

(72) Inventors: Krzysztof Palczewski, Bay Village, OH (US); Philip Kiser, Cleveland, OH (US); Jianye Zhang, Cleveland, OH (US); Mohsen Badiee, Shaker Heights, OH (US); Gregory Tochtrop, Shaker Heights, OH (US)

(73) Assignees: CASE WESTERN RESERVE UNIVERSITY, Cleveland, OH (US); THE UNITED STATES GOVERNMENT AS REPRESENTED BY THE DEPARTMENT OF VETERAN AFFAIRS, Washington, DC (US)

( * ) Notice: Subject to any disclaimer, the term of this patent is extended or adjusted under 35 U.S.C. 154(b) by 119 days.

(21) Appl. No.: 16/488,890

(22) PCT Filed: Feb. 27, 2018

(86) PCT No.: PCT/US2018/019944
§ 371 (c)(1),
(2) Date: Aug. 26, 2019

(87) PCT Pub. No.: WO2018/157129
PCT Pub. Date: Aug. 30, 2018

(65) Prior Publication Data
US 2020/0060996 A1  Feb. 27, 2020

Related U.S. Application Data

(60) Provisional application No. 62/463,936, filed on Feb. 27, 2017.

(51) Int. Cl.
*A61K 31/137* (2006.01)
*A61K 9/48* (2006.01)
*A61P 27/02* (2006.01)
*A61K 9/00* (2006.01)

(52) U.S. Cl.
CPC .......... *A61K 31/137* (2013.01); *A61K 9/0048* (2013.01); *A61P 27/02* (2018.01)

(58) Field of Classification Search
CPC ...... A61K 31/137; A61K 9/0048; A61P 27/02
See application file for complete search history.

(56) References Cited

U.S. PATENT DOCUMENTS

2013/0197096 A1* 8/2013 Scott ................ C07C 217/64
                                                              514/653
2014/0275043 A1  9/2014 Kuksa et al.
2014/0357611 A1  12/2014 Palczewski et al.

FOREIGN PATENT DOCUMENTS

WO  2009045479 A1  4/2009
WO  2009058216 A1  5/2009
WO  2013166449     11/2013

OTHER PUBLICATIONS

Substance Record for SID 55839820, Oct. 8, 2018, URL: <https://pubchem.ncbi.nim.nih.gov/substance/55839820/version/1#section=top>.
PUBCHEM; Substance Record for SID 55839820, Available Date: Oct. 8, 2018, [retrieved on May 14, 2018], Retrieved from the Internet: URL: https://pubchem.ncbi.nim.nih.gov/substance/55839820/version/1#section=top. entire document.
Applicant: Case Western Reserve University; PCT International Application No. PCT/US18/019944; PCT International Filing Date: Feb. 27, 2018; "Visual Cycle Modulators"; PCT International Search Report and Written Opinion; Authorized Officer: Blaine R. Copenheaver; Date of Completion: May 15, 2018; 10 pgs.
Applicant: Case Western Reserve University; European Application No. 18757135.1; "Visual Cycle Modulators"; Supplementary European Search Report; Date of Completion: Nov. 13, 2020; 16 pgs.
Philip D. Kiser, et al.; "Rational Tuning of Visual Cycle Modulator Pharmacodynamics"; Journal of Pharmacology and Experimental Therapeutics, vol. 362, No. 1, May 5, 2017, pp. 131-145, XP055745505, ISSN: 0022-3565, DOI: 10.1124/jpet.117.240721.
Applicant: Case Western Reserve University; Australian Application No. 2018223810; Australian Office Action dated Apr. 14, 2021; 9 pgs.
Applicant: Case Western Reserve University; European Application No. 18757135.1; Extended European Search Report dated Jul. 2, 2021; 19 pgs.

* cited by examiner

*Primary Examiner* — Jared Barsky
(74) *Attorney, Agent, or Firm* — Tarolli, Sundheim, Covell & Tummino LLP

(57) ABSTRACT

A method of treating an ocular disorder in a subject in need thereof includes administering to the subject a therapeutically effective amount of a retinal sequestering compound of formula (I).

5 Claims, 9 Drawing Sheets

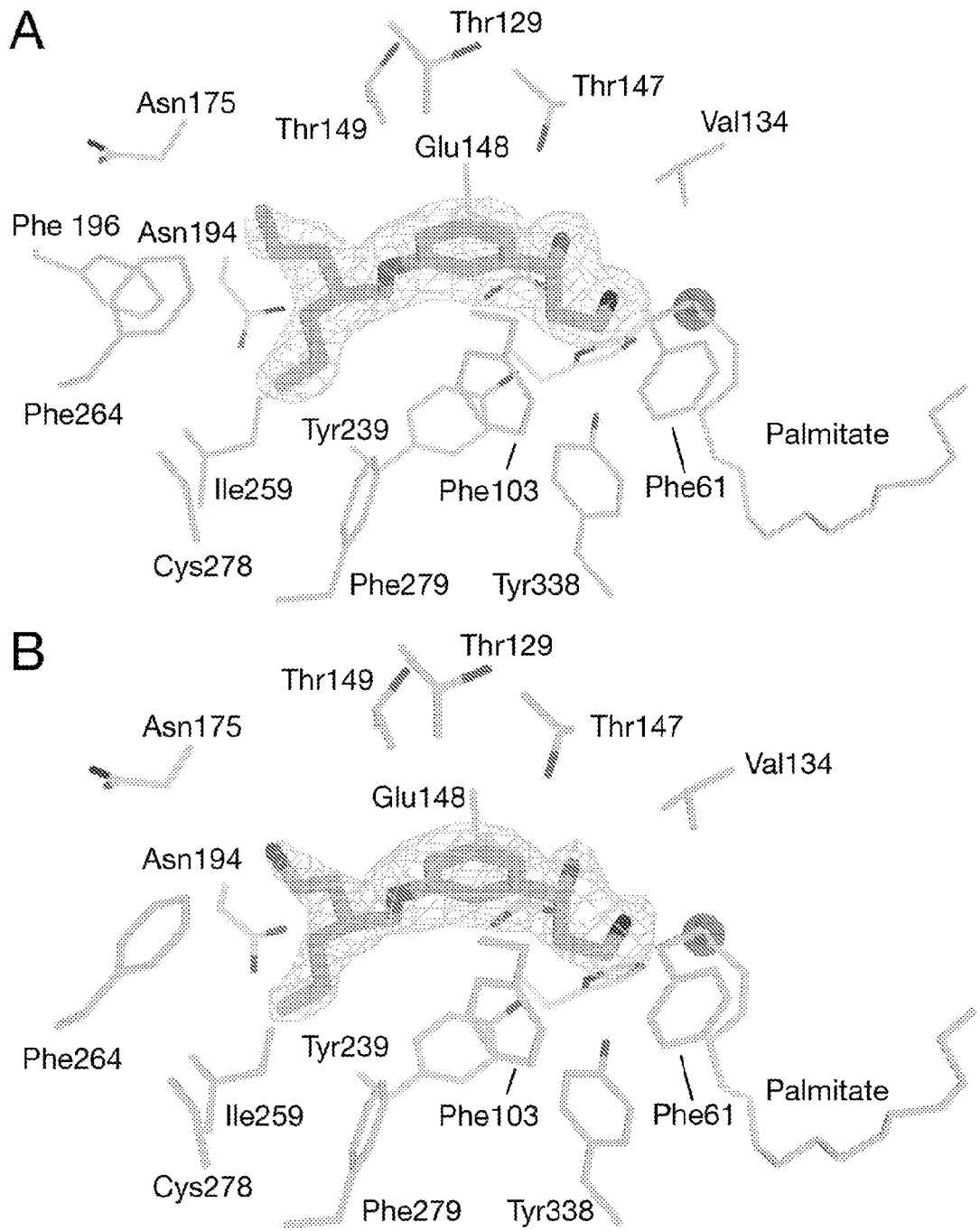
Figs. 2A-B

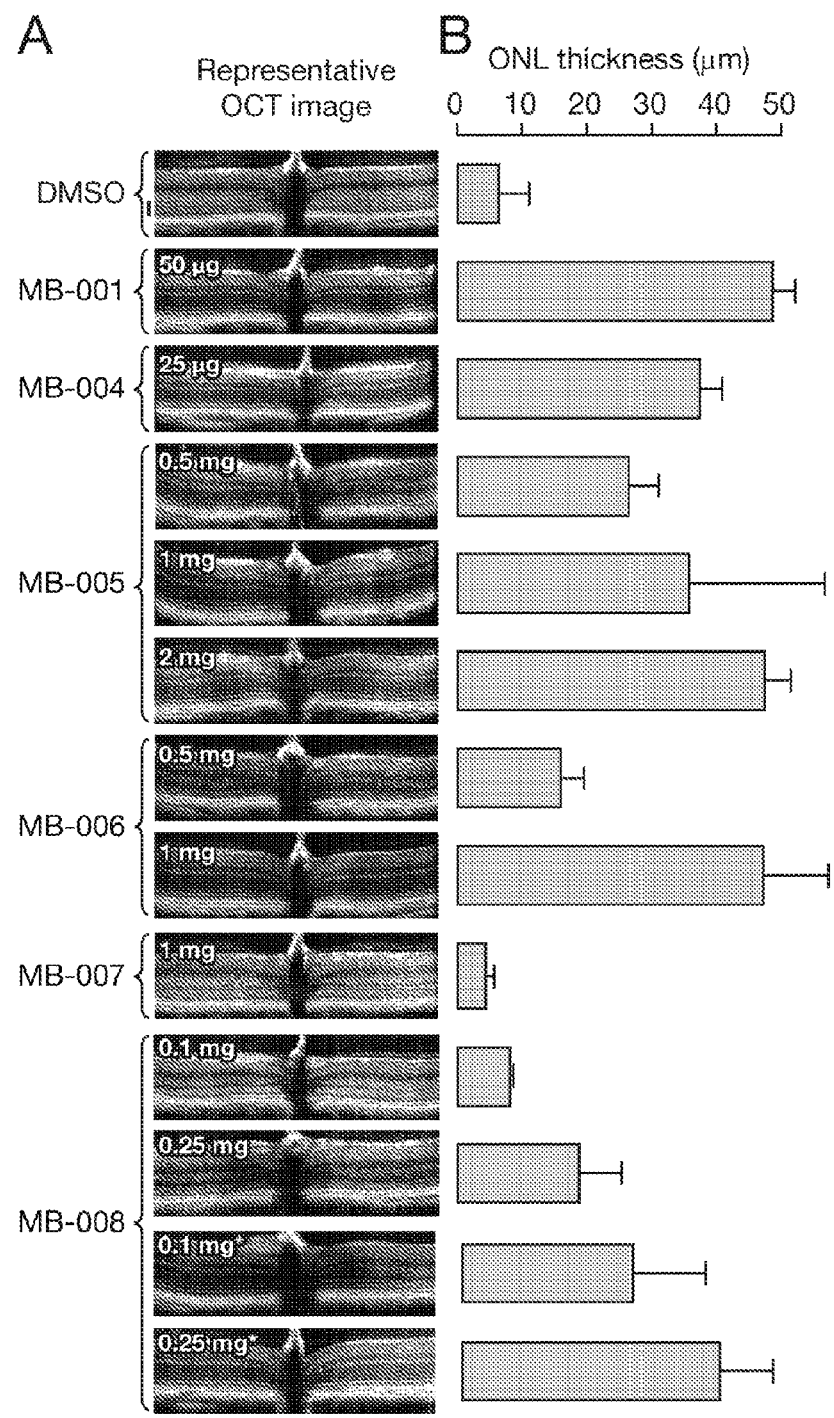
Figs. 7A-B

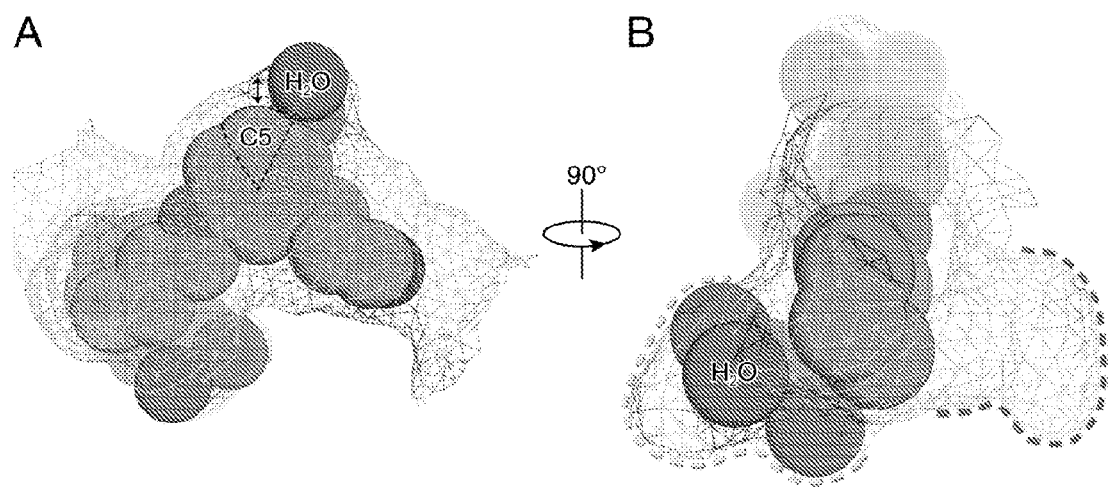
Figs. 8A-B

VISUAL CYCLE MODULATORS

RELATED APPLICATION

This application claims priority from U.S. Provisional Application No. 62/463,936 filed Feb. 27, 2017, the subject matter of which is incorporated herein by reference in its entirety.

GOVERNMENT FUNDING

This invention was made with government support under Grant Nos. EY009339, EY024864, P30EY011373, and P30EY025585, awarded by The National Institutes of Health. The United States government has certain rights to the invention.

BACKGROUND

Visual function in humans and other vertebrates relies critically on a vitamin A-derived molecule called retinaldehyde, which constitutes the chromophoric substance of rod and cone visual pigments. The efficacy of retinaldehyde in triggering light perception depends on it existing in an 11-cis configuration coupled to rod and cone opsins through a protonated imine (Schiff base) bond. Absorption of light by 11-cis-retinaldehyde stimulates its isomerization to an all-trans configuration with resultant conformational changes in the opsin molecule allowing it to trigger the phototransduction cascade with ensuing activation of retinal neurons and eventual stimulation of visual centers in the brain.

After several seconds, the photoactivated visual pigment releases all-trans-retinaldehyde which terminates signal transduction and leaves the opsin molecule insensitive to further light stimulation. Restoration of light sensitivity depends upon the conversion of all-trans-retinaldehyde back into the 11-cis form which can then conjugate with opsins to reform ground state visual pigments. The classic version of this process, known as the visual or retinoid cycle, is carried out by a group of enzymes and retinoid binding proteins located within and between the retinal pigment epithelium (RPE) and photoreceptor outer segments. Evidence is also mounting for an intra-retinal pathway involving Müiller glia that provides 11-cis-retinaldehyde selectively to cone photoreceptors.

Despite its essential function in initiating vision, retinaldehyde can cause retinal toxicity, a feature which has been implicated in diseases including Stargardt macular dystrophy and age-related macular degeneration (AMD). This toxicity stems in large part from its aldehyde functionality, which is reactive towards certain cellular nucleophiles including protein amino groups and phosphatidylethanolamine (PE). At concentrations easily achieved in vivo under strong lighting conditions retinaldehyde induces apoptosis in cultured cell lines. Mice deficient in ABCA4 and RDH8, key proteins involved in retinaldehyde clearance, are susceptible to light-induced retinal degeneration. These mice also accumulate autofluorescent material in their retinas, known as lipofuscin, that is partially composed of retinaldehyde-PE adducts, the best characterized of which is a compound called A2E.

SUMMARY

Embodiments described herein relate to retinal sequestering compounds that include primary amines for use in the treatment of diseases and disorders related to aberrant all-trans-retinal accumulation in a subject's ocular tissue. It has been discovered that all-trans-retinal, a retinoid metabolite naturally produced during visual processing, is highly toxic when present at elevated levels. To lower its toxicity, therapeutic retinal sequestering compounds that include primary amines have been identified in the Example below that can be delivered to and retained in the eye to modulate the visual (retinoid) cycle.

In some embodiments, the retinal sequestering compound for use in a method described herein can include the formula (I):

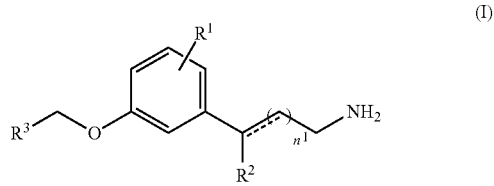

wherein $n^1$ is an integer from 1 to 6;
$R^1$ is H or a lipophilic or hydrophobic alkyl or fluoro alkyl group that includes at least three carbon atoms;
$R^2$ is H, $CH_3$, or OH;
$R^3$ is a substituted or unsubstituted $C_1$-$C_{12}$ alkyl, $C_2$-$C_{12}$ alkenyl, $C_2$-$C_{12}$ alkynyl, $C_3$-$C_6$ aryl, heteroaryl, heterocyclyl, or $C_6$-$C_{12}$ alkaryl, wherein $R^3$ is not a substituted or unsubstituted cycloalkyl, cycloalkenyl, heteroaryl, heterocyclyl, or branched alkyl if $R^1$ is H and $n^1$ is 1;
the dashed line is an optional bond; and
pharmaceutically acceptable salts thereof.

In other embodiments, $R^1$ does not include acidic or basic functional groups.

In other embodiments. $R^1$ is a branched or cyclic $C_3$-$C_{24}$ alkyl or fluoroalkyl.

In some embodiments, $R^1$ is selected from the group consisting of:

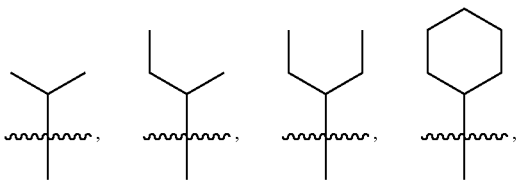

and fluoro derivatives thereof.

In other embodiments, $R^3$ is selected from the group consisting of:

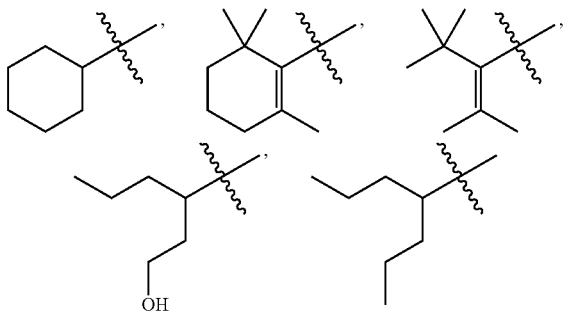

and fluoro derivatives thereof.

In some embodiments, the retinal sequestering compound for use in a method described herein can include the formula (II):

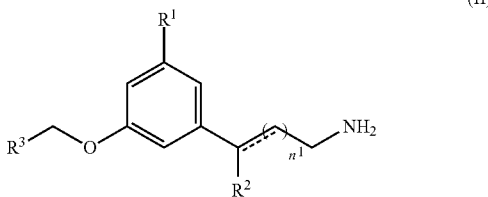

(II)

wherein $n^1$ is an integer from 1 to 6;

$R^1$ is a lipophilic or hydrophobic alkyl or fluoroalkyl group that includes at least three carbon atoms and is branched and/or cyclic;

$R^2$ is H, $CH_3$, or OH;

$R^3$ is a substituted or unsubstituted $C_1$-$C_{12}$ alkyl, $C_2$-$C_{12}$ alkenyl, $C_2$-$C_{12}$ alkynyl, $C_3$-$C_6$ aryl, heteroaryl, heterocyclyl, or $C_6$-$C_{12}$ alkaryl;

the dashed line is an optional bond; and pharmaceutically acceptable salts thereof.

In other embodiments, $R^1$ does not include acidic or basic functional groups.

In other embodiments, $R^1$ is a branched or cyclic $C_3$-$C_{24}$ alkyl or fluoroalkyl.

In some embodiments, $R^1$ is selected from the group consisting of:

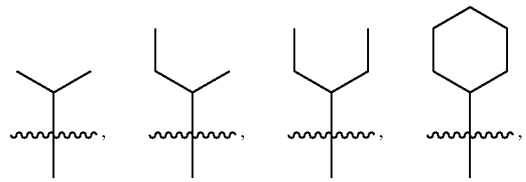

and fluoro derivatives thereof.

In other embodiments, $R^3$ is selected from the group consisting of:

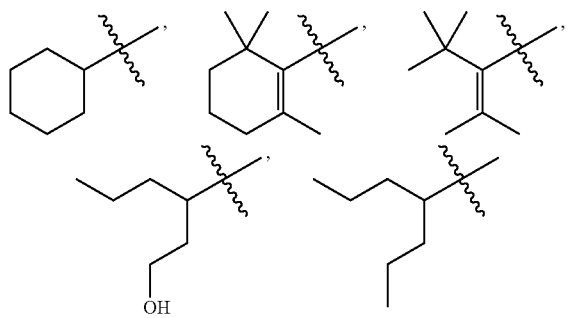

and fluoro derivatives thereof.

BRIEF DESCRIPTION OF THE DRAWINGS

FIGS. 2(A-B) illustrate binding of MB-004 and MB-008 to the RPE65 active site pocket. MB-004 (A) and MB-008 (B) are shown as sticks. Residues within 4.5 Å of the MB ligands are shown as sticks. The iron cofactor and the iron-bound palmitate ligand are shown as spheres and sticks, respectively. The mesh represents a σA-weighted $F_o$-$F_c$ electron density map calculated after deletion of the ligand and 30 cycles of REFMAC refinement. Residues within 4.5 Å of the ligand were harmonically restrained to their initial positions during refinement. The electron density suggested that the R, S form of MB-008, which was added to the protein as a racemic mixture, was the dominant isomer occupying the binding pocket.

FIGS. 7(A-B) illustrate protective effects of MB compounds against light-induced retinal degeneration in Abca4$^{-/-}$Rdh8$^{-/-}$ mice. Drugs were administrated at the indicated doses to 4-6 week-old Abca4$^{-/-}$Rdh8$^{-/-}$ mice (weight ~20 g) by oral gavage. After a 24 h dark adaptation, mice were exposed to 10,000 lux light for 30 min and then returned to a dark environment for 3 days. (A) Representative OCT images of mice treated with MB compounds. A dramatic decrease in the ONL indicates advanced retinal degeneration. The black scale beside the DMSO image represents 50 µm. (B) Retinal protective effects exerted by MB compounds as quantified by average ONL thickness. Only non-scattering ONL layers were measured. For images in which the ONL layer boundary was obscured due to light scattering, the ONL length was recorded as 0 µm. Error bars represent standard deviations; n=3-5 for each group.

FIGS. 8(A-B) illustrate structure of the emixustat-binding region of the RPE65 active site cavity. Ligands and water molecules are shown as van der Waals spheres with carbon, nitrogen and oxygen atoms. (A) A view from the active site entry port showing water-filled polar (left) and apolar (right) binding pockets, respectively delineated with blue and red dashed lines, on opposite sides of the emixustat cyclohexyl ring. (B) A view perpendicular to the plane of the phenyl ring showing the relatively snug fit of the phenyl ring in the vicinity of carbon 5 (C5) to the active site pocket. The emixustat molecule is shown as full scale van der Waals spheres and the surrounding binding pocket as its Connolly surface. This figure was generated using coordinates deposited under the PDB accession code 4RSC in PyMOL (Schrödinger, LLC).

DETAILED DESCRIPTION

Figure 1A:
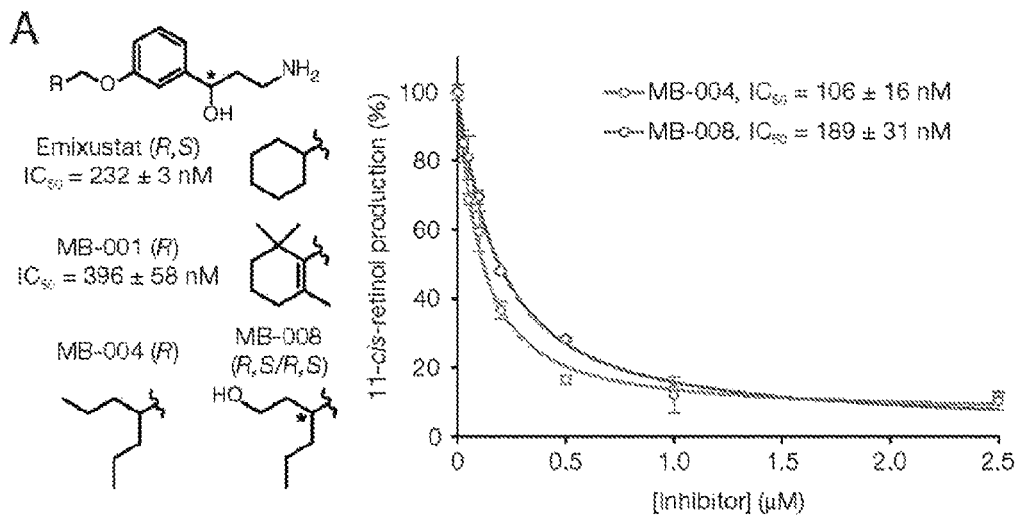
FIGS. 1(A-B) illustrate in vitro inhibition of retinoid isomerase activity by test (MB) compounds. Primary amines were pre-incubated with bovine RPE microsomes at room temperature for 5 min, then all-trans-retinol was added and the mixtures were incubated at 37° C. All incubation mixtures were quenched by the addition of methanol after 1 h of incubation. Inhibition of RPE65 enzymatic activity was measured as a decline in 11-cis-retinol production. (A) Production of 11-cis-retinol in the presence of amines designed to inhibit RPE65; (B) Production of 11-cis-retinol in the presence of bulky amines. The crystal structure of RPE65 with its inhibitors suggests that the inhibition potency of these amines could be marginal.

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

It will be noted that the structure of some of the compounds of the application include asymmetric (chiral) carbon atoms. It is to be understood accordingly that the isomers arising from such asymmetry are included within the scope of the invention, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" refers to compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

The term "chiral isomer" refers to a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n−1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric isomers" refer to the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Further, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative", refers to compounds that have a common core structure, and are substituted with various groups as described herein. For example, all of the compounds represented by formula I are primary amines and have formula I as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" refer to modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The term "treating" refers to inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" refers to stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term a "pharmaceutical composition" refers to a formulation containing the disclosed compounds in a form suitable for administration to a subject. The pharmaceutical composition can be in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including ocular, oral, pulmonary, rectal, parenteral, transdermal, subcutaneous, intravenous, intramuscular, intraperitoneal, intranasal, and the like. Dosage forms for the topical or transdermal administration of a compound of this invention include powders, sprays, ointments, pastes, creams, lotions, gels, solutions, patches and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" refers to a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" refers to compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" refers to pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated within the scope of the claims.

The phrase "pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of salts are found in Remington's Pharmaceutical Sciences, 18th ed. (Mack Publishing Company, 1990). For example, salts can include, but are not limited to, the hydrochloride and acetate salts of the aliphatic amine-containing, hydroxyl amine-containing, and imine-containing compounds of the present invention.

It should be understood that all references to pharmaceutically acceptable salts include solvent addition forms (solvates) or crystal forms (polymorphs) as defined herein, of the same salt.

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds of the present invention can be delivered in prodrug form. Thus, the present application is intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs the present invention are prepared by modifying functional groups present in the compound in such a way that the modifications are cleaved, either in routine manipulation or in vivo, to the parent compound. Prodrugs include compounds described herein wherein a hydroxy, amino, sulfhydryl, carboxy, or carbonyl group is bonded to any group that may be cleaved in vivo to form a free hydroxyl, free amino, free sulftydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds described herein, and the like (e.g., Bundegaard, H. "Design of Prodrugs" p 1-92, Elesevier, New York-Oxford (1985)).

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, $2^{nd}$ ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

The term "amine protecting group" refers to a functional group that converts an amine, amide, or other nitrogen-containing moiety into a different chemical group that is substantially inert to the conditions of a particular chemical reaction. Amine protecting groups can be removed easily and selectively in good yield under conditions that do not affect other functional groups of the molecule. Examples of amine protecting groups include, but are not limited to, formyl, acetyl, benzyl, t-butyldimethylsilyl, t-butdyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl) ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Other amine protecting groups can be identified by those of skill in the art.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" refers to solvent addition forms that contain either stoichiometric or non stoichiometric amounts of solvent. Some compounds have a tendency to trap a fixed molar ratio of solvent molecules in the crystalline solid state, thus forming a solvate. If the solvent is water, the solvate formed is a hydrate; when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertible by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g. an enolate); 3. protonation at a different position of the anion; Acid: 1. protonation; 2. formation of a delocalized cation; 3. deprotonation at a different position adjacent to the cation.

The term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

A "patient," "subject," or "host" to be treated by the subject method may mean either a human or non-human animal, such as primates, mammals, and vertebrates.

The term "prophylactic or therapeutic" treatment refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" refer to molecules and other agents that are biologically, physiologically, or pharmacologically active substances that act locally or systemically in a patient or subject to treat a disease or condition, such as retinal degeneration or other forms of retinal disease whose etiology involves elevated levels of all trans-retinal in the ocular tissue of a subject. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" refer to the dose of a drug, which produces 50% of its maximum response or effect, or alternatively, the dose, which produces a pre-determined response in 50% of test subjects or preparations. The term "LD50" refers to the dose of a drug, which is lethal in 50% of test subjects. The term "therapeutic index" refers to the therapeutic index of a drug, defined as LD50/ED50.

The term "substituted," as used herein, means that any one or more hydrogens on the designated atom is replaced with a selection from the indicated group, provided that the designated atom's normal valency is not exceeded, and that the substitution results in a stable compound. When the substituent is keto (i.e., =O), then 2 hydrogens on the atom are replaced. Ring double bonds, as used herein, are double bonds that are formed between two adjacent ring atoms (e.g., C=C, C=N, or N=N).

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), the invention is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

As used herein, "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)).

As used herein, "alkenyl" is intended to include hydrocarbon chains of either straight or branched configuration having one or more carbon-carbon double bonds occurring at any stable point along the chain. For example, $C_{2-6}$ alkenyl is intended to include $C_2$, $C_3$, $C_4$, $C_5$, and $C_6$ alkenyl groups. Examples of alkenyl include, but are not limited to, ethenyl and propenyl.

As used herein, "alkynyl" is intended to include hydrocarbon chains of either straight or branched configuration having one or more carbon-carbon triple bonds occurring at any stable point along the chain. For example, $C_{2-6}$ alkynyl is intended to include $C_2$, $C_3$, $C_4$, $C_5$, and $C_6$ alkynyl groups. Examples of alkynyl include, but are not limited to, ethynyl and propynyl.

Furthermore, "alkyl", "alkenyl", and "alkynyl" are intended to include moieties which are diradicals, i.e., having two points of attachment. A nonlimiting example of such an alkyl moiety that is a diradical is —CH$_2$CH$_2$—, i.e., a $C_2$ alkyl group that is covalently bonded via each terminal carbon atom to the remainder of the molecule.

"Aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and alkylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams such as azetidinones and pyrrolidinones, sultams, and sultones. Heterocyclic groups such as pyrrole and furan can have aromatic character. They include fused ring structures such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

As used herein, "halo" or "halogen" refers to fluoro, chloro, bromo, and iodo. "Counterion" is used to represent a small, negatively charged species such as fluoride, chloride, bromide, iodide, hydroxide, acetate, and sulfate.

"Stable compound" and "stable structure" are meant to indicate a compound that is sufficiently robust to survive isolation, and as appropriate, purification from a reaction mixture, and formulation into an efficacious therapeutic agent.

"Free compound" is used herein to describe a compound in the unbound state.

In the specification, the singular forms also include the plural, unless the context clearly dictates otherwise. Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

"Small molecule" refers to a molecule, which has a molecular weight of less than about 2000 amu, or less than about 1000 amu, and even less than about 500 amu.

All percentages and ratios used herein, unless otherwise indicated, are by weight.

The term "retina" refers to a region of the central nervous system with approximately 150 million neurons. It is located at the back of the eye where it rests upon a specialized epithelial tissue called retinal pigment epithelium or RPE. The retina initiates the first stage of visual processing by transducing visual stimuli in specialized neurons called "photoreceptors". Their synaptic outputs are processed by elaborate neural networks in the retina and then transmitted to the brain. The retina has evolved two specialized classes of photoreceptors to operate under a wide range of light conditions. "Rod" photoreceptors transduce visual images under low light conditions and mediate achromatic vision. "Cone" photoreceptors transduce visual images in dim to bright light conditions and mediate both color vision and high acuity vision.

Every photoreceptor is compartmentalized into two regions called the "outer" and "inner" segment. The inner segment is the neuronal cell body containing the cell nucleus. The inner segment survives for a lifetime in the absence of retinal disease. The outer segment is the region where the light sensitive visual pigment molecules are concentrated in a dense array of stacked membrane structures. Part of the outer segment is routinely shed and regrown in a diurnal process called outer segment renewal. Shed outer segments are ingested and metabolized by RPE cells.

The term "macula" refers to the central region of the retina, which contains the fovea where visual images are processed by long slender cones in high spatial detail ("visual acuity"). "Macular degeneration" is a form of retinal neurodegeneration, which attacks the macula and destroys high acuity vision in the center of the visual field. AMD can be in a "dry form" characterized by residual lysosomal granules called lipofuscin in RPE cells, and by extracellular deposits called "drusen". Drusen contain cellular waste products excreted by RPE cells. "Lipofuscin" and drusen can be detected clinically by ophthalmologists and quantified using fluorescence techniques. They can be the first clinical signs of macular degeneration.

Lipfuscin contains aggregations of A2E. Lipofuscin accumulates in RPE cells and poisons them by multiple known mechanisms. As RPE cells become poisoned, their biochemical activities decline and photoreceptors begin to degenerate. Extracellular drusen may further compromise RPE cells by interfering with their supply of vascular nutrients. Drusen also trigger inflammatory processes, which leads to choroidal neovascular invasions of the macula in one patient in ten who progresses to wet form AMD. Both the dry form and wet form progress to blindness.

The term "ERG" is an acronym for electroretinogram, which is the measurement of the electric field potential emitted by retinal neurons during their response to an experimentally defined light stimulus. ERG is a non-invasive measurement, which can be performed on either living subjects (human or animal) or a hemisected eye in solution that has been removed surgically from a living animal.

Embodiments described herein relate to retinal sequestering compounds that include primary amines for use in the treatment of diseases and disorders related to aberrant all-trans-retinal accumulation in a subject's ocular tissue. It has been discovered that all-trans-retinal, a retinoid metabolite naturally produced during visual processing, is highly toxic when present at elevated levels. To lower its toxicity, therapeutic retinal sequestering compounds that include primary amines have been identified in the Example below that can be delivered to and retained in the eye to modulate the visual (retinoid) cycle.

In some embodiments, the ocular disorder associated with aberrant all-trans-retinal accumulation in the ocular tissue of a subject can include, for example, retinal degeneration, macular degeneration, including age-related macular degeneration including the dry form and the wet form of age related macular degeneration, Stargardt's disease, Stargardt macular degeneration, fundus flavimaculatus, geographic atrophy, retinitis pigmentosa, ABCA4 mutation related retinal dystrophies, vitelliform (or Best) macular degeneration, adult onset form of vitelliform macular dystrophy, Sorsby's fundus dystrophy, Malattia leventinese (Doyne honeycomb or dominant radial drusen), diabetic retinopathy, diabetic maculopathy, diabetic macular edema, retinopathy that is or presents geographic atrophy and/or photoreceptor degeneration, retinopathy that is a lipofuscin-based retinal degeneration, aberrant modulation of lecithin-retinol acyltransferase in an eye, Leber's congenital amaurosis, retinal detachment, hemorrhagic retinopathy, hypertensive retinopathy, hereditary or non hereditary optic neuropathy, inflammatory retinal disease, retinal blood vessel occlusion, retinopathy of prematurity, ischemia reperfusion related retinal injury, proliferative vitreoretinopathy, retinal dystrophy, uveitis, retinal disorders associated with Alzheimer's disease, retinal disorders associated with multiple sclerosis, retinal disorders associated with Parkinson's disease, retinal disorders associated with viral infection (cytomegalovirus or herpes simplex virus), retinal disorders related to light overexposure or myopia, retinal disorders associated with AIDS, glaucoma, genetic retinal dystrophies, traumatic injuries to the optic nerve, such as by physical injury, excessive light exposure, or laser light, neuropathies due to a toxic agent or caused by adverse drug reactions or vitamin deficiency, progressive retinal atrophy or degeneration, retinal diseases or disorders resulting from mechanical injury, chemical or drug-induced injury, thermal injury, radiation injury, light injury, or laser injury, hereditary and non-hereditary retinal dystrophy, ophthalmic injuries from environmental factors, such as light-induced oxidative retinal damage, laser-induced retinal damage, "flash bomb injury," or "light dazzle", refractive errors including but not limited to myopia, and retinal diseases related to A2E accumulation including RDS/PHRP2-related macular degeneration, Batten disease (juvenile neuronal ceroid lipofuscinosis), and central serous chorioretinopathy.

Present at high micromolar levels, all-trans-retinal is uniquely concentrated in the eye and constitutes an ideal target for retinal sequestering compounds that do not interact with cellular machinery and processes. In certain embodiments, the primary amine containing compounds described herein do not inhibit enzymes, channels or receptors but instead react with all-trans-retinal. When administered to a subject, the primary amine containing compounds described herein transiently sequester all-trans-retinal in ocular tissue by forming a Schiff base and thus reduce peak concentrations of the toxic aldehyde. Because this reaction is readily reversible, there is no discernable diminution in the total amount of all-trans retinal needed for replenishment of the visual chromophore, 11-cis-retinal. In certain embodiments, the stability of the Schiff-bases formed from the retinal sequestering compounds should be such that the level of free all-trans-retinal in the ocular tissue of a subject is reduced to a level that is effective to mitigate retinal degeneration but not impair the normal retinoid cycle.

In some embodiments, the retinal sequestering compounds in accordance with the application do not inhibit or do not substantially inhibit RPE65 and/or LRAT enzymatic activity or any other proteins involved in retinoid metabolism in the eye of the subject. Inhibition of retinoid isomerase (RPE65) can produce the highly undesirable side effect of severely delayed dark adaptation. Therefore, in certain embodiments, the retinal sequestering compounds for use in a method described herein do not inhibit RPE65 and subsequently do not cause delayed dark adaptation (i.e., night blindness) in a subject.

In other embodiments, the retinal sequestering compounds in accordance with the application do inhibit or do substantially inhibit RPE65 and/or LRAT enzymatic activity or any other proteins involved in retinoid metabolism in the eye of the subject.

In an embodiment of the application, the retinal sequestering compounds that can inhibit retinal degeneration upon administration to a subject can be selected using an in vitro assays that measure the ability of a retinal sequestering compound to inhibit retinoid isomerase activity and sequester excessive all-trans-retinal in the ocular tissue and in vivo assays that measure, chromophore regeneration and ERG and the optical coherence tomography score of retinas of $Rdh8^{-/-}Abca4^{-/-}$ mice exposed to intense light-induced retinal degeneration. In certain embodiments, the retinal sequestering compounds that can inhibit retinal degeneration upon administration to a subject do not significantly inhibit RPE65 activity in a subject's ocular tissue. In other embodiments, the retinal sequestering compounds that can inhibit retinal degeneration upon administration to a subject do significantly inhibit RPE65 activity in a subject's ocular tissue. In some embodiments, retinal sequestering compounds when administered to a $Rdh8^{-/-}Abca4^{-/-}$ mouse increase the optical coherence tomography score of the mouse in comparison to untreated control animal. Additionally, in some embodiments, therapeutic efficacy of the retinal sequestering compounds of the application can be determined using an in vitro assay that measures the ability of a retinal sequestering compound to improve viability of RPE cells treated with retinal.

In some embodiments, the retinal sequestering compound for use in a method described herein can include the formula (I):

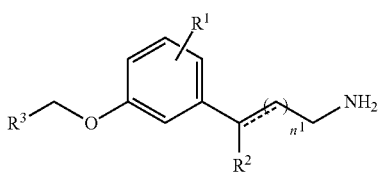

wherein $n^1$ is an integer from 1 to 6;

$R^1$ is H or a lipophilic or hydrophobic alkyl or fluoro alkyl group that includes at least three carbon atoms;

$R^2$ is H, $CH_3$, or OH;

$R^3$ is a substituted or unsubstituted $C_1$-$C_{12}$ alkyl, $C_2$-$C_{12}$ alkenyl, $C_2$-$C_{12}$ alkynyl, $C_3$-$C_6$ aryl, heteroaryl, heterocyclyl, or $C_6$-$C_{12}$ alkaryl, wherein $R^3$ is not a substituted or unsubstituted cycloalkyl, cycloalkenyl, heteroaryl, heterocyclyl, branched alkyl, or branched alkanol if $R^1$ is H and $n^1$ is 1;

the dashed line is an optional bond; and pharmaceutically acceptable salts thereof.

A lipophilic or hydrophobic alkyl group is one which associates with its own kind in an aqueous solution, not necessarily because the interactions between the lipophilic molecules are stronger than between the lipophilic molecule and water but because interactions between a lipophilic molecule and water would destroy the much stronger interactions between the water molecules themselves.

In other embodiments, $R^1$ does not include acidic or basic functional groups. Such groups would increase the binding interaction with the aqueous surroundings and hence lower the lipophilicity of the retinal sequestering compound.

In other embodiments, $R^1$ is a branched or cyclic $C_3$-$C_{24}$ alkyl or fluoroalkyl.

In some embodiments, $R^1$ is selected from the group consisting of:

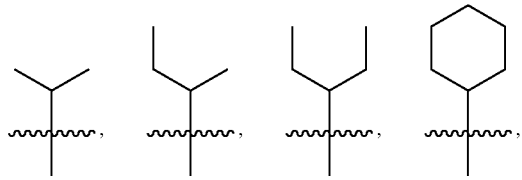

and fluoro derivatives thereof.

In other embodiments, $R^3$ is selected from the group consisting of:

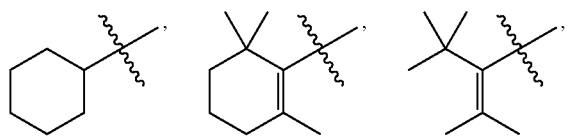

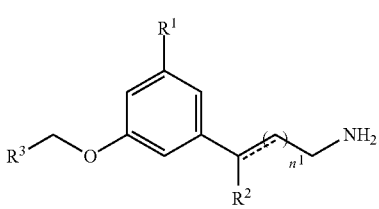

and fluoro derivatives thereof.

In other embodiments, the retinal sequestering compound for use in a method described herein can include the formula (II):

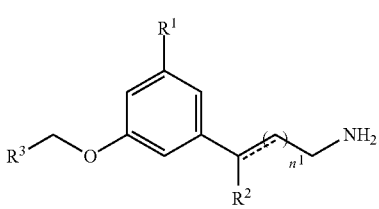

wherein $n^1$ is an integer from 1 to 6;

$R^1$ is a lipophilic or hydrophobic alkyl or fluoroalkyl group that includes at least three carbon atoms and is branched and/or cyclic;

$R^2$ is H, $CH_3$, or OH;

$R^3$ is a substituted or unsubstituted $C_1$-$C_{12}$ alkyl, $C_2$-$C_{12}$ alkenyl, $C_2$-$C_{12}$ alkynyl, $C_3$-$C_6$ aryl, heteroaryl, heterocyclyl, or $C_6$-$C_{12}$ alkaryl;

the dashed line is an optional bond; and pharmaceutically acceptable salts thereof.

In other embodiments, $R^1$ does not include acidic or basic functional groups.

In other embodiments, $R^1$ is a branched or cyclic $C_3$-$C_{24}$ alkyl or fluoroalkyl.

In some embodiments, $R^1$ is selected from the group consisting of:

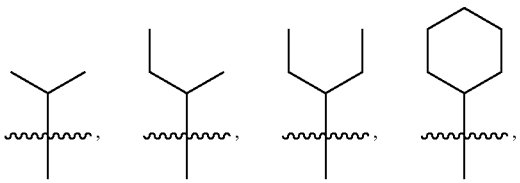

and fluoro derivatives thereof.

In other embodiments, $R^3$ is selected from the group consisting of:

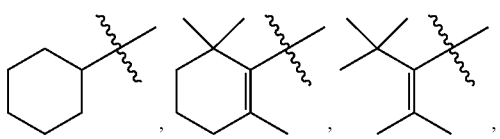

-continued

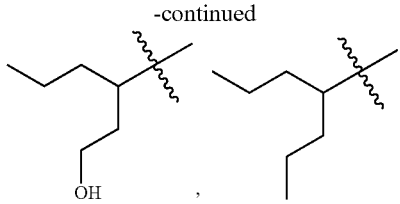

and fluoro derivatives thereof.

In other embodiments, the retinal sequestering compound for use in a method described herein can include the formula (III):

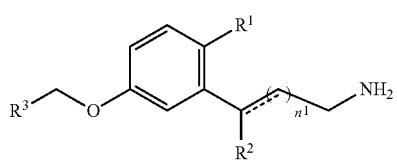
(III)

wherein $n^1$ is an integer from 1 to 6;
$R^1$ is a lipophilic or hydrophobic alkyl or fluoroalkyl group that includes at least three carbon atoms and is branched and/or cyclic;
$R^2$ is H, $CH_3$, or OH;
$R^3$ is a substituted or unsubstituted $C_1$-$C_{12}$ alkyl, $C_2$-$C_{12}$ alkenyl, $C_2$-$C_{12}$ alkynyl, $C_3$-$C_6$ aryl, heteroaryl, heterocyclyl, or $C_6$-$C_{12}$ alkaryl;
the dashed line is an optional bond; and
pharmaceutically acceptable salts thereof.

In other embodiments, $R^1$ does not include acidic or basic functional groups.

In other embodiments, $R^1$ is a branched or cyclic $C_3$-$C_{24}$ alkyl or fluoroalkyl.

In some embodiments, $R^1$ is selected from the group consisting of:

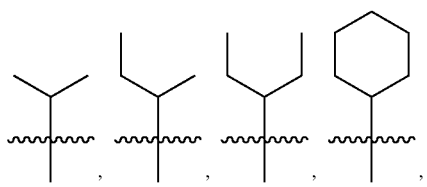

and fluoro derivatives thereof.

In other embodiments, $R^3$ is selected from the group consisting of:

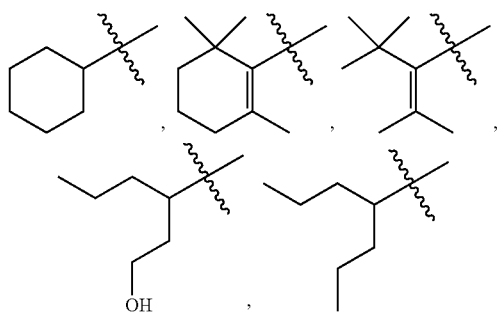

and fluoro derivatives thereof.

In other embodiments, the retinal sequestering compound for use in a method described herein can include the formula (IV):

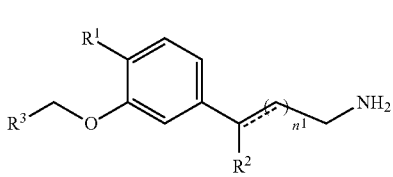
(IV)

wherein $n^1$ is an integer from 1 to 6;
$R^1$ is a lipophilic or hydrophobic alkyl or fluoroalkyl group that includes at least three carbon atoms and is branched and/or cyclic;
$R^2$ is H, $CH_3$, or OH;
$R^3$ is a substituted or unsubstituted $C_1$-$C_{12}$ alkyl, $C_2$-$C_{12}$ alkenyl, $C_2$-$C_{12}$ alkynyl, $C_3$-$C_6$ aryl, heteroaryl, heterocyclyl, or $C_6$-$C_{12}$ alkaryl;
the dashed line is an optional bond; and
pharmaceutically acceptable salts thereof.

In other embodiments, $R^1$ does not include acidic or basic functional groups.

In other embodiments, $R^1$ is a branched or cyclic $C_3$-$C_{24}$ alkyl or fluoroalkyl.

In some embodiments, $R^1$ is selected from the group consisting of:

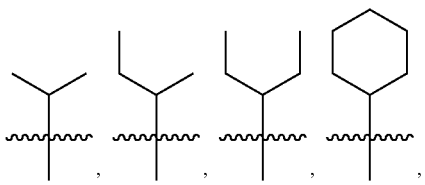

and fluoro derivatives thereof.

In other embodiments, $R^3$ is selected from the group consisting of:

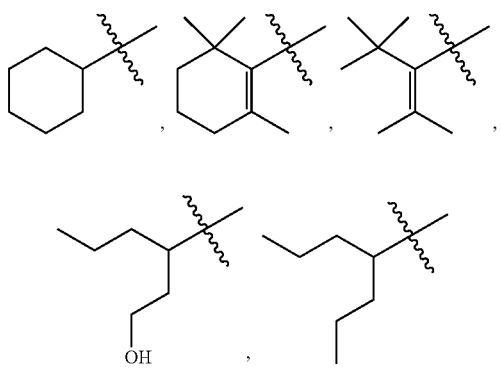

and fluoro derivatives thereof.

In other embodiments, the retinal sequestering compound for use in a method described herein can include the formula (V):

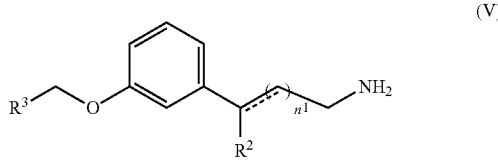

wherein $n^1$ is an integer from 2 to 6;
$R^2$ is H, $CH_3$, or OH;
$R^3$ is a substituted or unsubstituted $C_1$-$C_{12}$ alkyl, $C_2$-$C_{12}$ alkenyl, $C_2$-$C_{12}$ alkynyl, $C_3$-$C_6$ aryl, heteroaryl, heterocyclyl, or $C_6$-$C_{12}$ alkaryl;
the dashed line is an optional bond; and
pharmaceutically acceptable salts thereof.

In other embodiments, $R^3$ is selected from the group consisting of:

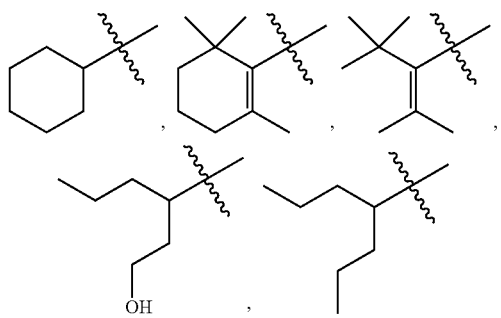

and fluoro derivatives thereof.

The retinal sequestering compounds used in methods described herein can be administered to the subject to treat the ocular disorder (e.g., macular degeneration or Stargardt disease) using standard delivery methods including, for example, ophthalmic, topical, parenteral, subcutaneous, intravenous, intraarticular, intrathecal, intramuscular, intraperitoneal, intradermal injections, or by transdermal, buccal, oromucosal, oral routes or via inhalation. The particular approach and dosage used for a particular subject depends on several factors including, for example, the general health, weight, and age of the subject. Based on factors such as these, a medical practitioner can select an appropriate approach to treatment.

Generally, the effective amount of the compound may be in the range of about 1 to 1,000 mg in the oral administration, about 0.1 to 500 mg in the intravenous administration, about 5 to 1,000 mg in the topical administration. Generally, the daily dosage for adults is in the range of about 0.1 to 5,000 mg, preferably about to 1,000 mg but cannot be determined uniformly because it depends on age, sex, body weight and the physical condition of the patients to be treated. The formulation may be administered once a day or several times a day with a divided dose Treatment according to the method described herein can be altered, stopped, or re-initiated in a subject depending on the status of ocular disorder. Treatment can be carried out as intervals determined to be appropriate by those skilled in the art. For example, the administration can be carried out 1, 2, 3, or 4 times a day. In another embodiment, the retinal sequestering compound can be administered after induction of macular degeneration has occurred.

The treatment methods can include administering to the subject a therapeutically effective amount of the retinal sequestering compound. Determination of a therapeutically effective amount is within the capability of those skilled in the art. The exact formulation, route of administration, and dosage can be chosen by the individual physician in view of the subject's condition.

Formulation of pharmaceutical compounds for use in the modes of administration noted above (and others) are described, for example, in Remington's Pharmaceutical Sciences (18th edition), ed. A. Gennaro, 1990, Mack Publishing Company, Easton, Pa. (also see, e.g., M. J. Rathbone, ed., Oral Mucosal Drug Delivery, Drugs and the Pharmaceutical Sciences Series, Marcel Dekker, Inc., N.Y., U.S.A., 1996; M. J. Rathbone et al., eds., Modified-Release Drug Delivery Technology, Drugs and the Pharmaceutical Sciences Series, Marcel Dekker, Inc., N.Y., U.S.A., 2003; Ghosh et al., eds., Drug Delivery to the Oral Cavity, Drugs and the Pharmaceutical Sciences Series, Marcel Dekker, Inc., N.Y. U.S.A., 1999.

In one example, the retinal sequestering compound can be provided in an ophthalmic preparation that can be administered to the subject's eye. The ophthalmic preparation can contain the retinal sequestering compound in a pharmaceutically acceptable solution, suspension or ointment. Some variations in concentration will necessarily occur, depending on the particular retinal sequestering compound employed, the condition of the subject to be treated and the like, and the person responsible for treatment will determine the most suitable concentration for the individual subject. The ophthalmic preparation can be in the form of a sterile aqueous solution containing, if desired, additional ingredients, for example, preservatives, buffers, tonicity agents, antioxidants, stabilizers, nonionic wetting or clarifying agents, and viscosity increasing agents.

Examples of preservatives for use in such a solution include benzalkonium chloride, benzethonium chloride, chlorobutanol, thimerosal and the like. Examples of buffers include boric acid, sodium and potassium bicarbonate, sodium and potassium borates, sodium and potassium carbonate, sodium acetate, and sodium biphosphate, in amounts sufficient to maintain the pH at between about pH 6 and about pH 8, and for example, between about pH 7 and about pH 7.5. Examples of tonicity agents are dextran 40, dextran 70, dextrose, glycerin, potassium chloride, propylene glycol, and sodium chloride.

Examples of antioxidants and stabilizers include sodium bisulfite, sodium metabisulfite, sodium thiosulfite, and thiourea. Examples of wetting and clarifying agents include polysorbate 80, polysorbate 20, poloxamer 282 and tyloxapol. Examples of viscosity-increasing agents include gelatin, glycerin, hydroxyethylcellulose, hydroxymethylpropylcellulose, lanolin, methylcellulose, petrolatum, polyethylene glycol, polyvinyl alcohol, polyvinylpyrrolidone, and carboxymethylcellulose. The ophthalmic preparation will be administered topically to the eye of the subject in need of treatment by conventional methods, for example, in the form of drops or by bathing the eye in the ophthalmic solution.

The retinal sequestering compound can also be formulated for topical administration through the skin. "Topical delivery systems" also include transdermal patches containing the ingredient to be administered. Delivery through the skin can further be achieved by iontophoresis or electrotransport, if desired.

Formulations for topical administration to the skin can include, for example, ointments, creams, gels and pastes comprising the retinal sequestering compound in a pharmaceutical acceptable carrier. The formulation of the retinal sequestering compound for topical use includes the preparation of oleaginous or water-soluble ointment bases, as is well known to those in the art. For example, these formulations may include vegetable oils, animal fats, and, for example, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

Subjects affected with or at risk of macular degeneration, which are not readily accessible or suitable for ophthalmic (e.g. eye-drops) and/or topical administration, can be treated by a systemic approach, such as oral, enteral, or intravenous infusion. For example, the retinal sequestering compound can be administered at a low dosage by continuous intravenous infusion.

In another example, in which a patient requires longer-term care, the retinal sequestering compound can be administered intermittently (e.g., every 12-24 hours). In a variation of this approach, the initial or loading dose can be followed by maintenance doses that are less than, (e.g., half) the loading dose or by continuous infusion. The duration of such treatment can be determined by those having skill in the art, based on factors, for example, the severity of the condition and the observation of improvements.

When administering the retinal sequestering compound to the subject by intravenous infusion, devices and equipment (e.g., catheters, such as central or peripheral venous catheters, tubing, drip chambers, flashback bulbs, injection Y sites, stopcocks, and infusion bags) can be used that are compatible with the retinal sequestering compound.

As discussed above, the retinal sequestering compounds may be administered to a subject in order to treat or prevent macular degeneration and other forms of retinal disease whose etiology involves elevated levels of toxic all-trans-retinal in a subject. Other diseases, disorders, or conditions characterized by increased or excessive all-trans-retinal in ocular tissue may be similarly treated.

In one embodiment, a subject is diagnosed as having symptoms of macular degeneration, and then a disclosed compound is administered. In another embodiment, a subject may be identified as being at risk for developing macular degeneration (risk factors include a history of smoking, age, female gender, and family history), and then a disclosed compound is administered. In another embodiment, a subject may have dry AMD in both eye, and then a disclosed compound is administered. In another embodiment, a subject may have wet AMD in one eye but dry AMD in the other eye, and then a disclosed compound is administered. In yet another embodiment, a subject may be diagnosed as having Stargardt disease and then a disclosed compound is administered. In another embodiment, a subject is diagnosed as having symptoms of other forms of retinal disease whose etiology involves increased all-trans-retinal in ocular tissue of a subject, and then the compound is administered. In another embodiment, a subject may be identified as being at risk for developing other forms of retinal disease whose etiology involves increased all-trans-retinal in ocular tissue, and then the disclosed compound is administered. In some embodiments, a compound is administered prophylactically. In some embodiments, a subject has been diagnosed as having the disease before retinal damage is apparent. In some embodiments, a human subject may know that he or she is in need of the macular generation treatment or prevention.

In some embodiments, a subject may be monitored for the extent of macular degeneration. A subject may be monitored in a variety of ways, such as by eye examination, dilated eye examination, fundoscopic examination, visual acuity test, and/or biopsy. Monitoring can be performed at a variety of times. For example, a subject may be monitored after a compound is administered. The monitoring can occur, for example, one day, one week, two weeks, one month, two months, six months, one year, two years, five years, or any other time period after the first administration of a compound. A subject can be repeatedly monitored. In some embodiments, the dose of a compound may be altered in response to monitoring.

In some embodiments, the disclosed methods may be combined with other methods for treating or preventing macular degeneration or other forms of retinal disease whose etiology involves increased all-trans-retinal in ocular tissue, such as photodynamic therapy. For example, a patient may be treated with more than one therapy for one or more diseases or disorders. For example, a patient may have one eye afflicted with dry form AMD, which is treated with a compound of the invention, and the other eye afflicted with wet form AMD, which is treated with, e.g., photodynamic therapy.

In yet another embodiment, the retinal sequestering compound described herein can be administered as part of a combinatorial therapy with additional therapeutic agents. The phrase "combinatorial therapy" or "combination therapy" embraces the administration of a retinal sequestering compound, and one or more therapeutic agents as part of a specific treatment regimen intended to provide beneficial effect from the co-action of these therapeutic agents. Administration of these therapeutic agents in combination typically is carried out over a defined period (usually minutes, hours, days or weeks depending upon the combination selected). "Combinatorial therapy" or "combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example by administering to the subject an individual dose having a fixed ratio of each therapeutic agent or in multiple, individual doses for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissue. The therapeutic agents can be administered by the same route or by different routes. The sequence in which the therapeutic agents are administered is not narrowly critical.

The invention is further illustrated by the following example, which is not intended to limit the scope of the claims.

Example

In this Example, we show that structure-guided modifications of the emixustat molecule result in retinal-sequestering compounds with varying affinities for the RPE65 active site. Agents with preferential retinal sequestering activity as well as RPE65 inhibitory activity both protected against retinal phototoxicity. These data suggest that the degree of RPE65 inhibition by visual cycle modulators can be tuned to maximize the therapeutic benefit of these compounds in the various ocular diseases.

Materials and Methods

Synthetic Chemistry

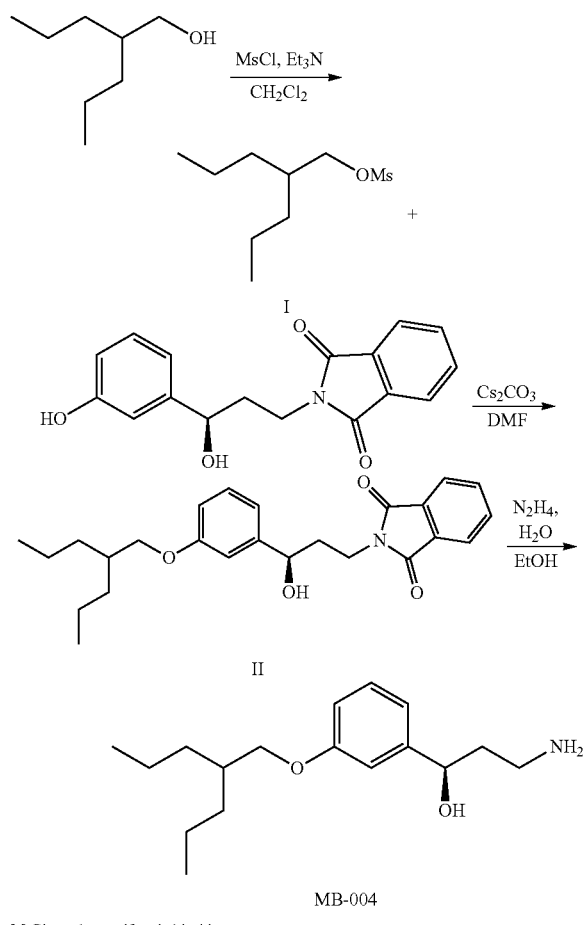

Scheme 1. Synthesis of MB-004

MsCl: methanesulfonyl chloride

2-Propylpentyl methanesulfonate (I)

An oven-dried 100 mL, two-necked, round-bottomed flask equipped with a magnetic stirring bar was sealed under argon with two rubber septa, one of which contained a needle adapter to an argon inlet. The flask was charged with anhydrous $CH_2Cl_2$ (32 mL), 2-propylpentan-1-ol (2.5 g, 19.2 mmol, 1.0 eq.) and triethylamine (2.9 g, 28.7 mmol, 1.5 eq.). This solution was cooled to 0° C. and then methanesulfonyl chloride (2.4 g, 21.1 mmol, 1.01 eq.) was added dropwise. The reaction mixture was warmed to room temperature over a period of 2 h. An aqueous solution of 1N HCl was added and the layers were separated. The organic layer was dried over $Na_2SO_4$ and concentrated under reduced pressure. Purification by silica gel column chromatography (EtOAc/Hexanes, 10:90) afforded 3.3 g (83%) of the desired product I as a pale yellow oil. $^1$H NMR (500 MHz, $CDCl_3$) δ 4.12 (d, J=5.5 Hz, 2H), 3.00 (s, 3H), 1.74 (p, J=5.5 Hz, 1H), 1.42-1.26 (m, 8H), 0.99-0.84 (m, 6H); $^{13}$C NMR (125 MHz, $CDCl_3$) δ 72.65, 37.45, 37.32, 33.06, 19.87, 14.40.

(R)-2-(3-Hydroxy-3-(3-((2-propylpentyl)oxy)phenyl)propyl)isoindoline-1,3-dione (II)

A dried round bottom flask equipped with a stir bar was sealed under argon. Then, it was charged with the phenol, prepared as described (40) (4.3 g, 14.4 mmol, 1.0 eq) in 85 ml anhydrous DMF. Anhydrous $Cs_2CO_3$ (6.4 g, 19.7 mmol, 1.4 eq.) was added to a stirred solution of phenol. Compound I (3.4 g, 16.4 mmol, 1.1 eq.) was added to the phenolate solution and the reaction mixture was stirred at 60° C. under argon for 24 h. The reaction mixture was partitioned between EtOAc and 25% $NH_4Cl$ (aq), and the aqueous layer was extracted with EtOAc. The combined organic layers were washed with brine, dried over anhydrous $MgSO_4$ and concentrated under reduced pressure. Purification by silica gel column chromatography (EtOAc/Hexanes, 30:70) afforded 2.3 g (40%) of the desired product II as a colorless oil. $^1$H NMR (500 MHz, $CDCl_3$) δ 7.86-7.82 (m, 2H), 7.74-7.70 (m, 2H), 7.18 (t, J=7.9 Hz, 1H), 6.91-6.89 (m, 1H), 6.88 (d, J=7.8 Hz, 1H), 6.73 (dd, J=8.2, 2.3 Hz, 1H), 4.66 (dd, J=8.1, 5.2 Hz, 1H), 3.91 (t, J=6.5 Hz, 2H), 3.80 (d, J=5.6 Hz, 2H), 2.12-2.06 (m, 2H), 1.81-1.74 (m, 1H), 1.45-1.30 (m, 8H), 0.94-0.88 (m, 6H); $^{13}$C NMR (125 MHz, $CDCl_3$) δ 168.94, 159.70, 145.29, 134.17, 132.18, 129.55, 123.46, 117.77, 113.76, 111.77, 71.41, 70.91, 37.71, 37.69, 35.05, 33.87, 20.14, and 14.60.

(R)-MB-004

An oven-dried one-necked, round-bottomed flask equipped with a magnetic stirring bar was charged with compound II (2.3 g, 5.9 mmol, 1.0 eq.), 150 ml EtOH and $N_2H_4 \cdot H_2O$ (1.6 ml, 50.9 mmol). The reaction mixture was stirred at room temperature for 24 h, then poured on filter paper and concentrated under reduced pressure. Purification by silica gel column chromatography ($NH_4OH$/MeOH/ $CH_2Cl_2$ 4:20:80) afforded 1.18 g (75%) of product as a colorless oil. $^1$H NMR (500 MHz, Methanol-$d_4$) δ 7.24 (t, J=7.9 Hz, 1H), 6.94 (s, 1H), 6.92 (d, J=7.8 Hz, 1H), 6.81 (d, J=8.3 Hz, 1H), 4.76 (t, J=6.6 Hz, 1H), 3.86 (d, J=5.4 Hz, 2H), 3.01-2.87 (m, 2H), 1.96 (q, J=6.9 Hz, 2H), 1.80 (p, J=5.7 Hz, 1H), 1.49-1.34 (m, 8H), 0.96-0.90 (m, 6H); $^{13}$C NMR (125 MHz, MeOD) δ 160.99, 147.46, 130.50, 118.86, 114.39, 112.95, 73.26, 71.76, 39.11, 39.05, 38.85, 34.93, 21.06, 14.78; ESI-HRMS: m/z calculated for $C_{17}H_{30}NO_2^+$ [M+H]$^+$: 280.22711, found: 280.22708.

Scheme 2. Synthesis of MB-005, MB-006, and MB-007.

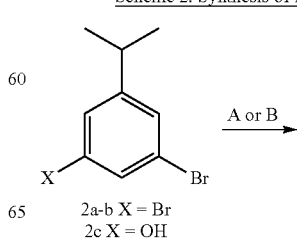

2a-b X = Br
2c X = OH

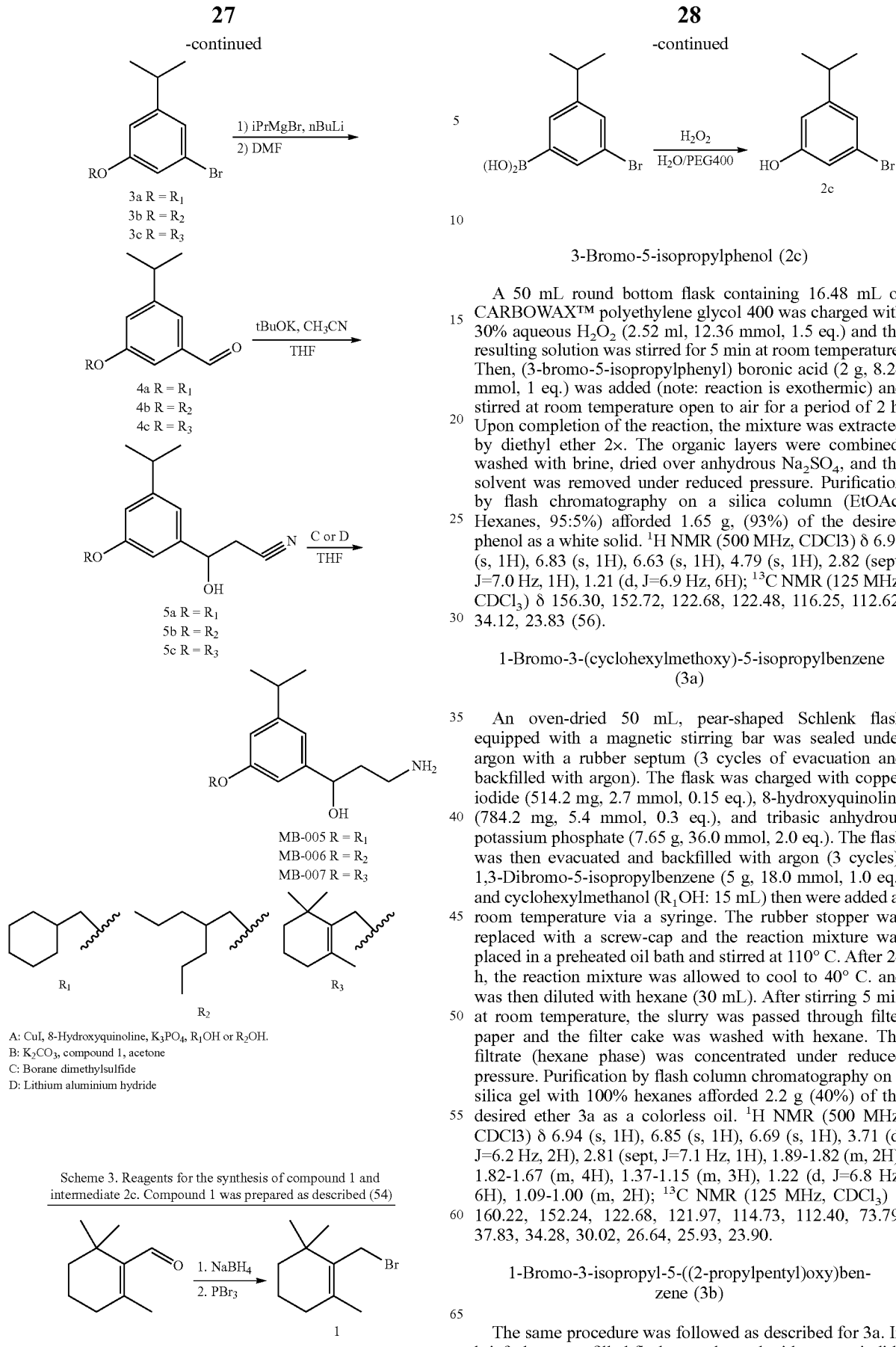

Scheme 3. Reagents for the synthesis of compound 1 and intermediate 2c. Compound 1 was prepared as described (54)

3-Bromo-5-isopropylphenol (2c)

A 50 mL round bottom flask containing 16.48 mL of CARBOWAX™ polyethylene glycol 400 was charged with 30% aqueous $H_2O_2$ (2.52 ml, 12.36 mmol, 1.5 eq.) and the resulting solution was stirred for 5 min at room temperature. Then, (3-bromo-5-isopropylphenyl) boronic acid (2 g, 8.24 mmol, 1 eq.) was added (note: reaction is exothermic) and stirred at room temperature open to air for a period of 2 h. Upon completion of the reaction, the mixture was extracted by diethyl ether 2×. The organic layers were combined, washed with brine, dried over anhydrous $Na_2SO_4$, and the solvent was removed under reduced pressure. Purification by flash chromatography on a silica column (EtOAc/Hexanes, 95:5%) afforded 1.65 g, (93%) of the desired phenol as a white solid. $^1$H NMR (500 MHz, CDCl3) δ 6.95 (s, 1H), 6.83 (s, 1H), 6.63 (s, 1H), 4.79 (s, 1H), 2.82 (sept, J=7.0 Hz, 1H), 1.21 (d, J=6.9 Hz, 6H); $^{13}$C NMR (125 MHz, $CDCl_3$) δ 156.30, 152.72, 122.68, 122.48, 116.25, 112.62, 34.12, 23.83 (56).

1-Bromo-3-(cyclohexylmethoxy)-5-isopropylbenzene (3a)

An oven-dried 50 mL, pear-shaped Schlenk flask equipped with a magnetic stirring bar was sealed under argon with a rubber septum (3 cycles of evacuation and backfilled with argon). The flask was charged with copper iodide (514.2 mg, 2.7 mmol, 0.15 eq.), 8-hydroxyquinoline (784.2 mg, 5.4 mmol, 0.3 eq.), and tribasic anhydrous potassium phosphate (7.65 g, 36.0 mmol, 2.0 eq.). The flask was then evacuated and backfilled with argon (3 cycles). 1,3-Dibromo-5-isopropylbenzene (5 g, 18.0 mmol, 1.0 eq.) and cyclohexylmethanol ($R_1$OH: 15 mL) then were added at room temperature via a syringe. The rubber stopper was replaced with a screw-cap and the reaction mixture was placed in a preheated oil bath and stirred at 110° C. After 24 h, the reaction mixture was allowed to cool to 40° C. and was then diluted with hexane (30 mL). After stirring 5 min at room temperature, the slurry was passed through filter paper and the filter cake was washed with hexane. The filtrate (hexane phase) was concentrated under reduced pressure. Purification by flash column chromatography on a silica gel with 100% hexanes afforded 2.2 g (40%) of the desired ether 3a as a colorless oil. $^1$H NMR (500 MHz, CDCl3) δ 6.94 (s, 1H), 6.85 (s, 1H), 6.69 (s, 1H), 3.71 (d, J=6.2 Hz, 2H), 2.81 (sept, J=7.1 Hz, 1H), 1.89-1.82 (m, 2H), 1.82-1.67 (m, 4H), 1.37-1.15 (m, 3H), 1.22 (d, J=6.8 Hz, 6H), 1.09-1.00 (m, 2H); $^{13}$C NMR (125 MHz, $CDCl_3$) δ 160.22, 152.24, 122.68, 121.97, 114.73, 112.40, 73.79, 37.83, 34.28, 30.02, 26.64, 25.93, 23.90.

1-Bromo-3-isopropyl-5-((2-propylpentyl)oxy)benzene (3b)

The same procedure was followed as described for 3a. In brief, the argon-filled flask was charged with copper iodide (514.2 mg), 8-hydroxyquinoline (784.2 mg), and tribasic anhydrous potassium phosphate (7.65 g). The flask was then evacuated and backfilled with argon (3 cycles). 1,3-Dibromo-5-isopropylbenzene (5 g) and 2-propylpentanol ($R_2OH$: 15 mL) were added. Purification by flash column chromatography on silica gel with 100% hexanes afforded 1.95 g (33%) of the desired ether 3b as a colorless oil. $^1H$ NMR (500 MHz, $CDCl_3$) δ 6.94 (s, 1H), 6.86 (s, 1H), 6.69 (s, 1H), 3.79 (d, J=5.6 Hz, 2H), 2.83 (sept, J=7.2 Hz, 1H), 1.79 (p, J=5.6 Hz, 1H), 1.47-1.31 (m, 8H), 1.23 (d, J=6.9 Hz, 6H), 0.92 (t, J=6.9 Hz, 6H); $^{13}C$ NMR (125 MHz, $CDCl_3$) δ 160.27, 152.21, 122.67, 121.92, 114.80, 112.35, 71.16, 37.67, 34.30, 33.82, 23.91, 20.14, 14.58.

1-Bromo-3-isopropyl-5-((2,6,6-trimethylcyclohex-1-en-1-yl)methoxy)benzene (3c)

An oven-dried 100 mL, three-necked, round-bottomed flask equipped with a magnetic stirring bar was sealed under argon with three rubber septa. The flask was charged with phenol 2c (1.83 g, 8.5 mmol, 1 eq.) and anhydrous $K_2CO_3$ (4.71 g, 34 mmol, 4 eq.). The flask was evacuated, filled up with argon twice and then charged with dry acetone (60 mL). Compound 1 (1.85 g, 8.5 mmol, 1.2 eq.) was then added this mixture. After refluxed under argon atmosphere for 24 h, the reaction mixture was cooled to room temperature, then filtered and concentrated under reduced pressure. Purification by flash chromatography on a silica column (100% Hexanes) afforded 2.4 g, (80%) of the desired ether 3c as a colorless oil. $^1H$ NMR (500 MHz, CDCl3) δ 6.96 (s, 1H), 6.93 (t, J=2.0 Hz, 1H), 6.75 (t, J=1.9 Hz, 1H), 4.39 (s, 2H), 2.83 (sept, J=6.9 Hz, 1H), 2.05 (t, J=6.3 Hz, 2H), 1.70 (s, 3H), 1.68-1.62 (m, 2H), 1.53-1.48 (m, 2H), 1.23 (d, J=6.9 Hz, 6H), 1.04 (s, 6H); $^{13}C$ NMR (125 MHz, $CDCl_3$) δ 160.12, 152.08, 136.07, 132.83, 122.50, 121.92, 114.63, 112.61, 64.66, 39.24, 34.15, 34.10, 32.88, 28.43, 23.77, 19.82, 19.27.

3-(Cyclohexylmethoxy)-5-isopropylbenzaldehyde (4a)

An oven-dried 50 mL, two-necked, round-bottomed flask was equipped with a magnetic stirring bar and sealed under argon with two rubber septa. The flask was charged with the aryl bromide (2.5 g, 8.0 mmol, 1.2 eq.) in anhydrous THF (8 mL). The reaction mixture was brought to 0° C., and a 3 M solution of isopropylmagnesium bromide in 2-Met-THF (3.3 mmol, 0.5 eq.) was added over 5 min and stirred for an additional 10 min. Then a 2.16 M solution of nBuLi in hexanes (6.7 mmol, 1.0 eq.) was added dropwise over 10 min while maintaining the temperature below 5° C. The resulting mixture was stirred at 0° C. for 1 h, cooled to −10° C., and dry DMF (670 uL, 8.9 mmol, 1.3 eq.) in dry THF (9 mL) was added dropwise over 10 min. The resulting mixture was warmed to rt over 1 h, then was added to a 0.5 M citric acid solution (30 mL). After 10 min stirring, the phases were separated and the aqueous phase was extracted one additional time with toluene. The combined organic phases were concentrated and water was removed azeotropically with toluene. Purification by flash chromatography on a silica column ($Et_2O$/Hexanes 7:93%) afforded 1.9 g, (90%) of the desired aldehyde 4a as a colorless oil. $^1H$ NMR (500 MHz, Chloroform-d) δ 9.94 (s, 1H), 7.32 (s, 1H), 7.19 (s, 1H), 7.05 (s, 1H), 3.80 (d, J=6.3, 2H), 2.95 (sept, J=7.2, 6.8 Hz, 1H), 1.92-1.85 (m, 2H), 1.84-1.67 (m, 4H), 1.36-1.17 (m, 3H), 1.28 (d, J=6.9 Hz, 6H), 1.12-1.02 (m, 2H); $^{13}C$ NMR (125 MHz, $CDCl_3$) δ 192.72, 160.10, 151.52, 137.92, 121.84, 120.66, 110.20, 73.87, 37.83, 34.12, 30.03, 26.63, 25.93, 23.92.

3-(Cyclohexylmethoxy)-5-isopropylbenzaldehyde (4b)

The same procedure was followed as described for 4a. At 0° C., a 3 M solution of isopropylmagnesium bromide in 2-Met-THF (2.9 mmol, 0.5 eq.) was added to a solution of the aryl bromide (2.27 g, 6.94 mmol, 1.2 eq.) in anhydrous THF (6.94 mL). Then, a 2.16 M solution of nBuLi in hexanes (5.9 mmol, 1.0 eq.) was added and followed by addition a solution of dry DMF (584 uL, 7.74 mmol, 1.3 eq.) in dry THF (7.74 mL) at −10° C. Purification by flash chromatography on a silica column ($Et_2O$/Hexanes 7:93%) afforded 1.7 g, (90%) of the desired aldehyde 4b as a colorless oil. $^1H$ NMR (500 MHz, CDCl3) δ 9.95 (s, 1H), 7.32 (s, 1H), 7.21 (s, 1H), 7.05 (s, 1H), 3.88 (d, J=5.3 Hz, 2H), 2.95 (sept, J=7.1 Hz, 1H), 1.82 (p, J=5.8 Hz, 1H), 1.50-1.32 (m, 8H), 1.28 (d, J=7.0 Hz, 6H), 0.95-0.89 (m, 6H); $^{13}C$ NMR (125 MHz, $CDCl_3$) δ 192.64, 160.14, 151.47, 137.92, 121.74, 120.58, 110.27, 71.25, 37.66, 34.13, 33.82, 23.91, 20.13, 14.56.

3-Isopropyl-5-((2,6,6-trimethylcyclohex-1-en-1-yl)methoxy)benzaldehyde (4c)

The same procedure was followed as described for 4a. At 0° C., a 3 M solution of isopropylmagnesium bromide in 2-Met-THF (1.75 mmol, 0.5 eq.) was added to a solution of the aryl bromide (1.47 g, 4.2 mmol, 1.2 eq.) in anhydrous THF (5 mL). Then, a 2.16 M solution of nBuLi in hexanes (3.5 mmol, 1.0 eq.) was added and followed by addition of a solution of dry DMF (343 uL, 4.54 mmol, 1.3 eq.) in dry THF (4.5 mL) at −10° C. Purification by flash chromatography on a silica column ($Et_2O$/Hexanes 5:95%) afforded 1.1 g, (87%) of the desired aldehyde 4c as a colorless oil. $^1H$ NMR (500 MHz, CDCl3) δ 9.96 (s, 1H), 7.34 (t, J=1.5 Hz, 1H), 7.29 (dd, J=2.6, 1.3 Hz, 1H), 7.11 (t, J=2.1 Hz, 1H), 4.48 (s, 2H), 2.96 (sept, J=6.9 Hz, 1H), 2.06 (t, J=6.3 Hz, 2H), 1.72 (s, 3H), 1.69-1.63 (m, 2H), 1.54-1.49 (m, 2H), 1.28 (d, J=6.9 Hz, 6H), 1.06 (s, 6H); $^{13}C$ NMR (125 MHz, $CDCl_3$) δ 192.74, 160.13, 151.50, 137.91, 136.29, 132.99, 122.11, 121.06, 110.04, 64.89, 39.39, 34.27, 34.13, 33.03, 28.58, 23.93, 19.98, 19.41.

3-(3-(Cyclohexylmethoxy)-5-isopropylphenyl)-3-hydroxypropanenitrile (5a)

An oven-dried 50 mL, two-necked, round-bottomed flask equipped with a magnetic stirring bar and sealed under argon with two rubber septa, one of which contained a needle adapter to an argon inlet. The flask was charged with anhydrous THF (9 mL) and anhydrous acetonitrile (290 uL, 5.2 mmol, 1.01 eq.), cooled to −42° C., and treated dropwise with a solution of potassium tert-butoxide (630 mg, 5.7 mmol, 1.12 eq.) in THF (6 mL). After stirring for 45 min, benzaldehyde (1.3 g, 5 mmol, 1.0 eq.) in THF (2.7 mL) also was added dropwise. The reaction was allowed to warm to −15° C. over a 4 h period and was quenched by the slow addition of 25% $NH_4Cl$ (aq) (1 mL). The layers were partitioned and the aqueous phase was extracted twice with EtOAc. The combined organic layers were washed with $H_2O$ (2×), brine, dried over $MgSO_4$, and concentrated under reduced pressure. Purification by flash column chromatography on silica gel (EtOAc/Hexanes 35:65) afforded 1.3 g (86%) of the nitrile 5a as a pale yellow oil. $^1$H NMR (500 MHz, Chloroform-d) δ 6.80 (s, 1H), 6.75 (s, 2H), 4.99 (t, J=6.3 Hz, 1H), 3.75 (d, J=6.1 Hz, 2H), 2.87 (sept, J=6.6 Hz, 1H), 2.78-2.74 (m, 2H), 1.90-1.83 (m, 2H), 1.81-1.66 (m, 4H), 1.36-1.25 (m, 3H), 1.23 (d, J=6.7 Hz, 6H), 1.11-1.01 (m, 2H); $^{13}$C NMR (125 MHz, CDCl$_3$) δ 160.03, 151.56, 142.52, 117.48, 115.89, 113.49, 108.61, 73.67, 70.59, 37.93, 34.41, 30.08, 28.04, 26.65, 25.95, 24.06, 24.01.

3-(3-(Cyclohexylmethoxy)-5-isopropylphenyl)-3-hydprxpropanenitrile (5b)

The same procedure was followed as described for 5a. A solution of potassium tert-butoxide (770 mg, 6.9 mmol, 1.12 eq.) in THF (7.5 mL) was added to a solution of anhydrous acetonitrile (356 uL, 6.4 mmol, 1.04 eq.) in anhydrous THF (9 mL) at –42° C. Then, benzaldehyde (1.7 g, 6.2 mmol, 1.0 eq.) in THF (6 mL) was added dropwise yielding the nitrile 5c (1.7 g, 87%) as a pale yellow oil. $^1$H NMR (500 MHz, CDCl3) δ 6.80 (s, 1H), 6.75 (s, 2H), 4.99 (t, J=6.4 Hz, 1H), 3.82 (d, J=5.5 Hz, 2H), 2.88 (sept, J=7.3 Hz, 1H), 2.79-2.75 (m, 2H), 2.30 (bs, 1H), 1.86-1.75 (m, 1H), 1.48-1.32 (m, 8H), 1.24 (d, J=6.7 Hz, 6H), 0.92 (t, J=6.8 Hz, 6H); $^{13}$C NMR (125 MHz, CDCl$_3$) δ 159.95, 151.39, 142.37, 117.35, 115.71, 113.30, 108.55, 70.89, 70.47, 37.60, 34.29, 33.72, 27.90, 23.93, 23.88, 20.03, 14.45.

3-Hydroxy-3-(3-isopropyl-5-((2,6,6-trimethylcyclohex-1-en-1-yl)methoxy)phenyl)propanenitrile (5c)

The same procedure was followed as described for 5a. A solution of potassium tert-butoxide (485 mg, 4.32 mmol, 1.12 eq.) in THF (10 mL) was added to a solution of anhydrous acetonitrile (222 uL, 4.2 mmol, 1.1 eq.) in anhydrous THF (8.4 mL) at –42° C. Then, benzaldehyde (1.16 g, 3.9 mmol, 1.0 eq.) in THF (4 mL) was added dropwise. Purification by flash column chromatography on silica gel (EtOAc/Hexanes 35:65) afforded 0.9 g (69%) of desired nitrile 5c as a pale yellow oil. $^1$H NMR (500 MHz, CDCl3) δ 6.84-6.82 (m, 2H), 6.82-6.80 (m, 1H), 5.01 (t, J=6.3 Hz, 1H), 4.43 (s, 2H), 2.89 (sept, J=6.8 Hz, 1H), 2.80-2.76 (m, 2H), 2.29 (s, 1H), 2.05 (d, J=6.3 Hz, 2H), 1.71 (s, 3H), 1.69-1.62 (m, 2H), 1.54-1.48 (m, 2H), 1.25 (d, J=6.9 Hz, 6H), 1.05 (s, 6H); $^{13}$C NMR (125 MHz, CDCl$_3$) δ 160.08, 151.53, 142.47, 136.06, 133.13, 117.51, 116.00, 113.81, 108.75, 70.66, 64.64, 39.40, 34.44, 34.26, 33.02, 28.60, 28.04, 24.08, 24.03, 19.99, 19.42.

3-Amino-1-(3-(cyclohexylmethoxy)-5-isopropylphenyl)propan-1-ol (MB-005)

An oven-dried 50 ml, two-necked, round-bottomed flask equipped with a magnetic stirring bar was sealed under argon with two rubber septa, one of which contained a needle adapter to an argon inlet. The flask was charged with anhydrous THF (14 mL) and nitrile 5a (1.3 g, 4.3 mmol, 1.0 eq.). To the stirred reaction mixture at room temperature, a 5.0 M solution of borane dimethyl sulfide complex in diethylether (10.8 mmol, 2.5 eq.) was added slowly. Then the reaction mixture was heated under reflux for 4 h. The reaction mixture was cooled to 0° C. and methanol was slowly added to decompose the unreacted borane complex. The organic solvent was evaporated under reduced pressure. Purification by silica gel column chromatography (NH$_4$OH/MeOH/CHCl$_3$ 4:20:80) afforded 0.6 g (46%) of MB-005 as a pale yellow oil. $^1$H NMR (500 MHz, CDCl$_3$) δ 6.79 (s, 1H), 6.76 (s, 1H), 6.66 (s, 1H), 4.90 (dd, J=8.8, 3.1 Hz, 1H), 3.75 (d, J=6.5 Hz, 2H), 3.18-3.08 (m, 1H), 3.03-2.93 (m, 1H), 2.85 (sept, J=7.0 Hz, 1H), 1.93-1.84 (m, 2H), 1.83-1.65 (m, 4H), 1.37-1.14 (m, 3H), 1.23 (d, J=6.7 Hz, 6H), 1.11-0.98 (m, 2H); $^{13}$C NMR (125 MHz, CDCl$_3$) δ 159.63, 150.60, 146.42, 116.21, 111.88, 108.74, 75.67, 73.54, 51.05, 40.65, 39.50, 38.00, 34.42, 30.14, 26.71, 26.00, 24.17, 24.10; ESI-HRMS: m/z calculated for C$_{19}$H$_{32}$NO$_2$$^+$ [M+H]$^+$: 306.24276; found: 306.24576.

3-Amino-1-(3-(cyclohexylmethoxy)-5-isopropylphenyl)propan-1-ol (MB-006)

The same procedure was followed as described for MB-005. A 2.0 M solution of borane dimethyl sulfide complex in diethylether (10.25 mmol, 2.5 eq.) was added to a solution of the nitrile 5b (1.3 g, 4.1 mmol, 1.0 eq.) in anhydrous THF (10 mL). Purification by silica gel column chromatography (NH$_4$OH/MeOH/CH$_2$Cl$_2$ 4:10:90) afforded 0.63 g (47%) of MB-006 as a pale yellow oil. $^1$H NMR (500 MHz, CDCl3) δ 6.79 (s, 1H), 6.74 (s, 1H), 6.65 (s, 1H), 4.90 (t, J=6.2 Hz, 1H), 3.81 (d, J=5.6 Hz, 2H), 3.23-3.14 (m, 1H), 3.12-3.01 (m, 1H), 2.84 (sept, J=7.3 Hz, 1H), 1.94 (q, J=6.0 Hz, 2H), 1.81-1.72 (m, 1H), 1.49-1.27 (m, 8H), 1.22 (d, J=6.6 Hz, 6H), 0.90 (t, J=6.9 Hz, 6H); $^{13}$C NMR (125 MHz, CDCl$_3$) δ 159.74, 150.68, 145.86, 116.17, 111.91, 108.93, 74.99, 70.89, 40.09, 38.01, 37.80, 34.42, 33.88, 24.16, 24.11, 20.16, 14.61; ESI-HRMS: m/z calculated for C$_{20}$H$_{36}$NO$_2$$^+$ [M+H]$^+$: 322.27406; found: 322.27402.

3-Amino-1-(3-isopropyl-5-((2,6,6-trimethylcyclohex-1-en-1-yl)methoxy)phenyl)propan-1-ol (MB-007)

An oven-dried 50 mL, two-necked, round-bottomed flask equipped with a magnetic stirring bar was sealed under argon with two rubber septa, one of which contained a needle adapter to an argon inlet. The flask was charged with anhydrous THF (25 mL) and a 2.0 M solution of LiAlH$_4$ in THF (3.68 μL, 7.36 mmol, 2.5 eq). At 0° C., a solution of nitrile 5c (1 g, 2.9 mmol, 1 eq) in anhydrous THF (6 mL) was then added dropwise to this reaction mixture. The resulting yellow mixture was stirred at 0° C. for 1 h. At 0° C., the reaction was quenched by slow addition of H$_2$O (366 uL) (caution: with evolution of hydrogen gas) followed sequentially by 15% w/v aq. NaOH (366 μL) and H$_2$O (1.1 mL). Then, the sludge was stirred for 10 min at room temperature. The resulting mixture was vacuum filtered and washed well with CH$_2$Cl$_2$. The filtrate was dried over MgSO$_4$ and concentrated under reduced pressure. Purification by flash chromatography on a silica column (NH$_4$OH/MeOH/CH$_2$Cl$_2$ 4:10:90-6:20:80) afforded 0.6 g (60%) of MB-007 as a colorless oil. $^1$H NMR (500 MHz, CDCl$_3$) δ 6.87-6.79 (m, 2H), 6.73 (t, J=1.9 Hz, 1H), 4.92 (dd, J=8.8, 3.2 Hz, 1H), 4.43 (s, 2H), 3.19-3.10 (m, 1H), 3.03-2.94 (m, 1H), 2.87 (sept, J=6.9 Hz, 1H), 2.04 (t, J=6.3 Hz, 2H), 1.94-1.76 (m, 2H), 1.71 (s, 3H), 1.68-1.61 (m, 2H), 1.53-1.47 (m, 2H), 1.24 (d, J=6.9 Hz, 6H), 1.05 (s, 6H); $^{13}$C NMR (125 MHz, CDCl$_3$) δ 159.55, 150.35, 146.26, 135.56, 133.31, 116.20, 112.18, 108.71, 76.77, 75.66, 64.34, 40.64, 39.53, 39.30, 34.29, 34.13, 32.88, 28.46, 24.03, 23.96, 19.86, 19.32. ESI-HRMS: m/z calculated for C$_{22}$H$_{36}$NO$_2$$^+$ [M+H]$^+$: 346.27406, found 346.27399.

Scheme 4. Reagents and conditions for the synthesis of MB-008

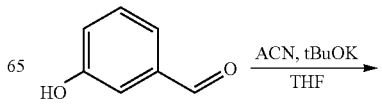

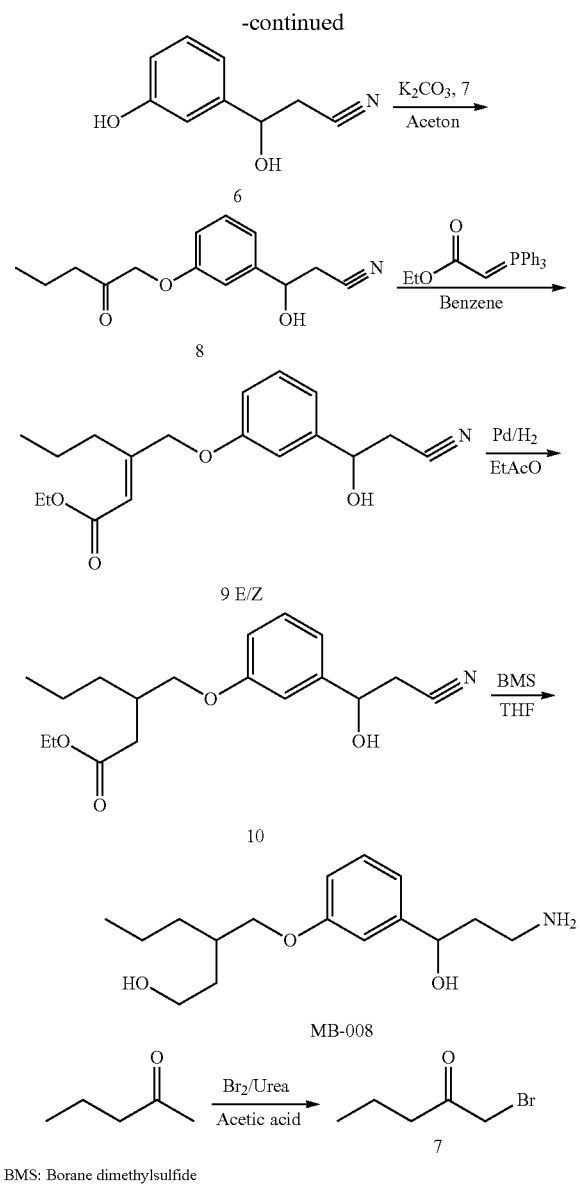

BMS: Borane dimethylsulfide

3-Hydroxy-3-(3-hydroxyphenyl)propanenitrile (6)

An oven-dried 100 mL, two-necked, round-bottomed flask was sealed under argon. The flask was charged with anhydrous THF (11 mL) and anhydrous acetonitrile (465 µL, 8.3 mmol), cooled to −42° C. and a solution of potassium tert-butoxide (2.06 g, 18.4 mmol) in THF (20 mL) was added dropwise. After stirring for 45 min at −42° C., 3-hydroxy-benzaldehyde (1 g, 8.2 mmol) in THF (4.5 mL) was added dropwise. The reaction was allowed to warm to −15° C. over a 4 h period, and then was quenched by the slow addition of 25% NH$_4$Cl (aq) (14.5 mL). The layers were partitioned, and the aqueous phase was extracted 2× with EtOAc. The combined organic layers were washed with H$_2$O (2×), brine, dried over MgSO$_4$, and evaporated under reduced pressure. Purification by silica gel column chromatography (EtOAc/Hexanes 50:50) afforded 1.06 g (80%) of product 6 as a pale yellow oil. $^1$H NMR (400 MHz, CDCl$_3$) δ 7.26 (t, 1H, J=8 Hz), 6.95-6.91 (m, 2H), 6.82 (ddd, 1H, J=1.2, 2.4, 8.0 Hz), 5.01 (t, 1H, J=6.4 Hz), 2.77 (d, 2H, J=6 Hz) ppm; $^1$H NMR values matched reported literature values (59). $^{13}$C NMR (100 MHz, CDCl$_3$) δ 156.5, 143.0, 130.4, 117.7, 117.4, 116.0, 112.5, 68.1, 25.7 ppm.

1-Bromopentan-2-one (7)

An oven-dried 100 mL, two-necked, round-bottomed flask was charged with urea (9.8 g, 163.2 mmol, 1.63 eq.), acetic acid (39 mL), and 2-pentanone (10.65 mL, 100 mmol, 1 eq.). At 0° C., Br$_2$ (5.46 ml, 17.05 g, 107.2 mmol, 1.07 eq.) was added to the mixture and stirred at 18-20° C. until the red color disappeared (~4.5 h). This mixture was then diluted with water (150 mL) and extracted with CH$_2$Cl$_2$. The extract was washed with aqueous sodium carbonate, dried over MgSO$_4$, and concentrated by rotary evaporation (caution: product is a lachrymator, so it needs to be handled carefully). Purification by silica gel column chromatography (Et$_2$O/Hexanes 3:97) afforded 4.2 g (26%) of 1-bromopentan-2-one as a pale yellow liquid (60). $^1$H NMR (500 MHz, CDCl$_3$) δ 3.90 (s, 2H), 2.66 (t, J=7.2 Hz, 2H), 1.67 (h, J=7.5 Hz, 2H), 0.96 (t, J=7.2 Hz, 3H); $^{13}$C NMR (125 MHz, CDCl$_3$) δ 202.25, 41.85, 34.44, 17.50, 13.72.

3-Hydroxy-3-(3-((2-oxopentyl)oxy)phenyl)propa-nenitrile (8)

An oven-dried 100 mL, two-necked, round-bottomed flask equipped with stir bar was sealed under argon. The flask was charged with the substituted phenol (566 mg, 3.5 mmole, 1.1 eq.), 1-bromo-2-pentanone 7 (520 mg, 3.2 mmole, 1 eq.), anhydrous potassium carbonate (646.8 mg. 4.68 mmol, 1.3 eq.), and dry acetone (32 mL). The reaction mixture was refluxed for 24 h under argon atmosphere. The resulting slurry was cooled down, treated with water, and extracted with ether (3×). The combined ether extracts were washed with 2.5M NaOH aq solution, brine, dried over MgSO$_4$ and evaporated under reduced pressure. Purification by silica gel column chromatography (EtOAc/Hexanes 50:50) afforded 570 mg (73%) of product 8 as a pale yellow oil (61). $^1$H NMR (500 MHz, CDCl$_3$) δ 7.32 (t, J=7.8 Hz, 1H), 7.01 (d, J=7.2 Hz, 1H), 6.97 (s, 1H), 6.85 (dd, J=8.2, 2.6 Hz, 1H), 5.03 (t, J=6.2 Hz, 1H), 4.57 (s, 2H), 2.76 (d, J=6.1 Hz, 2H), 2.56 (t, J=7.3 Hz, 2H), 1.67 (h, J=7.7 Hz, 2H), 0.95 (t, J=7.7 Hz, 3H); $^{13}$C NMR (125 MHz, CDCl$_3$) δ 207.10, 158.28, 142.91, 130.29, 118.70, 117.05, 114.68, 111.94, 72.74, 69.94, 40.96, 27.95, 16.69, 13.73.

Ethyl (E)-3-((3-(2-cyano-1-hydroxyethyl)phenoxy)methyl)hex-2-enoate (9)

An oven-dried 100 mL, two-necked, round-bottomed flask equipped with a magnetic stirring bar was sealed under argon. The flask was charged with the ketone 8 (389.0 mg, 1.57 mmol, 1 eq.) and anhydrous benzene (40 mL), followed by addition of (ethoxycarbonylmethylene)triphenyl phosphorane (75.9 mg, 0.218 mmol, 1.09 eq.). This reaction mixture was refluxed under argon for 8 h at 84° C. Then, the solution was cooled down to room temperature and concentrated under reduced pressure. Purification by silica gel column chromatography (EtOAc/Hexanes 35:65) afforded 274 mg (55%) of E/Z mixture of products 9 as a colorless oil. It was used for next step without further characterization.

Ethyl 3-((3-(2-cyano-1-hydroxyethyl)phenoxy)methyl)hexanoate (10)

An oven-dried 25 mL, two-necked, round-bottomed flask equipped with a magnetic stirring bar was sealed under argon. The flask was charged with EtOAc (12 mL) and the alkene 9 (223 mg, 0.7 mmol, 1 eq.). To the stirred mixture, palladium on carbon (75 mg, 10% wt, 0.07 mmol, 0.1 eq.) was added. The flask was evacuated in mild vacuum and refilled with hydrogen. Hydrogenation was carried out via a double balloon overnight at 25° C. Then, the reaction mixture was filtered through a pad of celite and the filtrate was concentrated under reduced pressure. Purification by silica gel column chromatography (EtOAc/Hexanes 30:70) afforded 200 mg (89%) of product 10 as a colorless oil (62). $^1$H NMR (500 MHz, CDCl$_3$) δ 7.28 (t, J=7.8 Hz, 1H), 6.94 (s, 2H), 6.85 (dd, J=8.3, 2.5 Hz, 1H), 4.99 (t, J=6.2 Hz, 1H), 4.12 (q, J=7.2 Hz, 2H), 3.96-3.91 (m, 1H), 3.90-3.84 (m, 1H), 2.75 (d, J=5.5 Hz, 2H), 2.63 (brs, 1H), 2.52-2.44 (m, 1H), 2.41-2.31 (m, 2H), 1.55-1.45 (m, 1H), 1.41-1.34 (m, 3H), 1.24 (t, J=7.1 Hz, 3H), 0.92 (t, J=6.8 Hz, 3H); $^{13}$C NMR (125 MHz, CDCl$_3$) δ 173.07, 159.44, 142.70, 129.98, 117.70, 117.29, 114.75, 111.62, 70.18, 70.06, 60.41, 36.66, 35.07, 33.53, 27.91, 20.01, 14.24, 14.22.

3-((3-(3-Amino-1-hydroxypropyl)phenoxy)methyl)hexan-1-ol (MB-008)

An oven-dried 10 ml, two-necked, round-bottomed flask was sealed under argon. The flask was charged with anhydrous THF (5 mL) and the nitrile 10 (40 mg, 0.125 mmol, 1 eq.). To the stirred reaction mixture at room temperature, borane methyl sulfide complex 5M in ether (125 uL, 0.626 mmol, 5 eq.) was slowly added. After complete addition, the reaction mixture was refluxed (2-4 h) and then cooled to 0° C. The unreacted borane complex was decomposed with addition of methanol. The organic solvent was evaporated under reduced pressure, and purification of the residue by silica gel column chromatography (NH$_4$OH/MeOH/CH$_2$Cl$_2$ 10:20:80) afforded 20.5 mg (90%) of MB-008 (a mixture of four stereoisomers) as a pale yellow oil. $^1$H NMR (500 MHz, CD$_3$OD) δ 7.22 (t, J=7.9 Hz, 1H), 6.97-6.88 (m, 2H), 6.80 (dd, J=8.2, 2.4 Hz, 1H), 4.71 (dd, J=7.9, 5.3 Hz, 1H), 3.90 (d, J=5.4 Hz, 2H), 3.66 (t, J=6.9 Hz, 2H), 2.84-2.71 (m, 2H), 1.96 (h, J=5.6 Hz, 1H), 1.92-1.81 (m, 2H), 1.77-1.59 (m, 2H), 1.55-1.35 (m, 4H), 0.94 (t, J=6.9 Hz, 3H); $^{13}$C NMR (125 MHz, CD$_3$OD) δ 160.85, 147.98, 130.36, 119.08, 114.29, 112.98, 73.44, 71.68, 61.04, 41.97, 39.50, 36.03, 35.67, 35.07, 21.05, 14.73. ESI-HRMS: m/z calculated for $C_{16}H_{28}NO_3^+$ [M+H]$^+$: 282.20637, found 282.20633.

Biochemical Procedures
Retinoid Isomerase Activity Assays

Bovine RPE microsomes were prepared as previously described to provide the isomerase for the assay. Synthesized primary amine (1 µl in DMF, with the final concentration ranging between 50 nM and 50 µM) was added to 10 mM Bis-Tris propane/HCl buffer, pH 7.4, containing 150 µg RPE microsomes, 1% BSA, 1 mM disodium pyrophosphate, and 20 µM aporetinaldehyde-binding protein 1 (CRALBP). The resulting mixture was pre-incubated at room temperature for 5 min. Then, all-trans-retinol (1 µl in DMF, at a final concentration of 20 µM) was added. The resulting mixture was incubated at 37° C. for 1 h. The reaction was quenched by adding 300 µl methanol, and products were extracted with 300 µl hexanes. Production of 11-cis-retinol was quantified by normal-phase HPLC with 10% (v/v) EtOAc in hexanes as the eluent at a flow rate of 1.4 ml/min. Retinoids were detected by monitoring their absorbance at 325 nm and quantified based on a standard curve representing the relationship between the amount of synthetic 11-cis-retinol standard and the area under the corresponding chromatographic peak.

Mouse Handling and Drug Administration

Abca4$^{-/-}$Rdh8$^{-/-}$ mice on a C57BL/6J background were generated as previously described. Male and female WT mice with C57BL/6J backgrounds were obtained from The Jackson Laboratory. Abca4$^{-/-}$Rdh8$^{-/-}$ mice used in this study were homozygous for the Leu450 allele of Rpe65 as determined by a genotyping protocol published previously and free of Crb1/rd8 and rd/rd mutations. Animals were housed either in the animal facility at the Case Western Reserve University School of Medicine, where they received a standard chow diet (LabDiet 5053) and were maintained under a 12-h light (~300 lux) and 12-h dark cycle or at the Cole Eye Institute animal facility where they were. Mice were dark adapted overnight prior to all experiments. A cohort of Rdh8$^{-/-}$Abca4$^{-/-}$ or C57BL/6J mice was used when they reached the age of 1 to 2 months, and both sexes were used evenly. All tested primary amines were suspended in 100 µl soybean oil with less than 10% (v/v) DMSO and were administered by oral gavage with a 22-gauge feeding needle. Experimental manipulations in the dark were done under dim red light transmitted through a Kodak No. 1 Safelight Filter (transmittance >560 nm).

Induction of Acute Retinal Degeneration in Abca4$^{-/-}$Rdh8$^{-/-}$ Mice

After dark adaptation for 24 h, Abca4$^{-/-}$Rdh8$^{-/-}$ mice with pupils dilated by 1% tropicamide were exposed to fluorescent light (10,000 lux; 150 W spiral lamp; Commercial Electric) for 30 min in a white paper bucket (Papersmith) and then kept in the dark for an additional 3 days. Development of retinal degeneration was then determined by ultra-high-resolution spectral domain OCT (SD-OCT; Bioptigen) and ERG as previously described.

Quantification of MB-005 in Mouse Eyes

MB-005 (1 mg/mouse) was administrated by oral gavage to C57BL/6J mice, which were then kept in the dark for 4-24 h. Then, mice were euthanized, and their eyes were homogenized in 1 ml of 10 mM sodium phosphate buffer, pH 7.4, containing 50% methanol (v/v). The resulting mixture was extracted with 4 ml EtOAc. Extracts were dried in vacuo and reconstituted in 400 µl ethanol containing 1 nmol emixustat as the internal standard. This solution (100 µl) was analyzed by liquid chromatography-electrospray ionization-MS/MS (LC-ESI-MS/MS) (4.6 mm×150 mm; Agilent ZORBAX Eclipse XDB-C18) with a gradient of acetonitrile in water (0%-100% in 30 min) as the eluent at a flow rate of 0.5 ml/min. Amounts of amines were quantified based on a standard curve representing the relationship between the amount of MB005 and the ratio of corresponding peak areas of MB005 to emixustat.

Visual Chromophore Recovery Assay

After bright light exposure resulting in photoactivation of 95% of rhodopsin, mice were kept in the dark for 6 h. Then, the animals were euthanized and their eyes were collected and homogenized in 10 mM sodium phosphate buffer, pH 7.4, containing 50% methanol (v/v) and 40 mM hydroxylamine. The resulting mixture was extracted with 4 ml of hexanes. Extracts were dried in vacuo, reconstituted in 300 µl of hexanes, and 100 µl of the extract was injected into an HPLC system for analysis with 10% (v/v) EtOAc in hexanes as the eluent. Amounts of 11-cis-retinal were quantified based on a standard curve representing the relationship between the amount of 11-cis-retinyl oxime and the area under the corresponding chromatographic peak.

In Vivo ERG Recordings

C57BL/6J mice aged 1.5-4 months were anesthetized with ketamine (80 mg/kg) and xylazine (16 mg/kg) after overnight dark adaptation. Mydriatic eye drops were used to dilate the pupil (1% tropicamide; 2.5% phenylephrine). ERGs were obtained using an active electrode that contacted the corneal surface; needle electrodes placed in the cheek and tail provided reference and ground leads, respectively. Strobe stimuli were presented to the dark-adapted eye in an LKC (Gaithersburg, Md.) ganzfeld. Responses were amplified, averaged and stored using an LKC UTAS E-3000 signal averaging system.

Baseline dark-adapted ERGs were recorded from each mouse. After a minimum 1 day interval, MB compounds or vehicle were administered by gavage at 9 a.m. The next morning, mydriatic eye drops were used to dilate the pupils and mice were then exposed to a 10-minute 10,000 lux bleach. Mice were dark-adapted for 6 hours, after which ERGs were recorded.

Identification atRAL Conjugates with MB Compounds in Abca4$^{-/-}$Rdh8$^{-/-}$ Mice MB-005 or MB-006 (50 mg/kg) were administered by oral gavage to Abca4$^{-/-}$Rdh8$^{-/-}$ mice 24 h prior to light exposure. After exposure to fluorescent light for 10 min, animals were euthanized and their eyes were collected and homogenized in acetonitrile. After centrifugation, the supernatant was concentrated to 400 μl under vacuum. Extracts (100 μl) were injected into an LXQ linear ion trap mass spectrometer (Thermo Scientific) coupled to an Agilent 1100 HPLC system (Agilent Technologies). Separation of retinylidene Schiff bases was achieved on a reverse phase C18 Phenomenex HPLC column (250×4.60 mm; 5 μm) in a linear gradient of acetonitrile in water of 50% to 100% within 30 min at a flow rate of 1.5 ml/min. All solvents contained 0.1% formic acid (v/v). The HPLC effluent was directed into the mass spectrometer via an atmospheric pressure chemical ionization (APCI) interface operated in the positive ionization mode. Identification of a retinylidene Schiff base was achieved by comparing its mass spectrum with that of an authentic standard.

Statistics

Data representing the means±SD for the results of at least 3 independent experiments were compared by 1-way ANOVA. Differences with P values of less than 0.05 were considered statistically significant.

Study Approval

All animal procedures and experiments were approved by the Case Western Reserve University Animal Care Committee and conformed to recommendations of the American Veterinary Medical Association Panel on Euthanasia and the Association for Research in Vision and Ophthalmology.

RPE65 Purification and Crystallization

RPE65 was purified from bovine RPE microsomes using the detergent $C_8E_6$ (Anatrace, Mowmee, Ohio) as previously described. Inhibitors were added to the protein sample at the time of detergent solubilization as well as after concentrating the purified protein in both cases to a final concentration of 1 μM. Inhibitors were delivered to the samples as 100 mM DMSO stock solutions. Crystallization was accomplished by mixing 1-2 μL of the concentrated protein sample with 1-2 μL of crystallization solution consisting of 40% (v/v) PEG 300, 100 mM CHES-NaOH, pH 9.5, and 200 mM NaCl or 30% v/v PEG 400, 100 mM CAPS-NaOH, pH 10.5, 500 mM $(NH_4)_2SO_4$ and 10% v/v glycerol (Conditions #26 and #27, respectively of the Wizard Cryo screen, Rigaku). Crystals appeared in one or two days and grew to maximal dimensions of 75×75×300 μm within one month. Mature crystals were harvested with Microloops (Mitegen), flash cooled and stored in liquid nitrogen prior to X-ray exposure.

Collection and Processing of X-Ray Diffraction Data and Structure Refinement

X-ray diffraction data sets were collected at the NE-CAT ID-C and ID-E beamlines at the Advanced Photon Source. Diffraction data were indexed, integrated and scaled with XDS. Data from three separate crystals of the RPE65/MB-004 complex were merged using XSCALE to boost the signal-to-noise ratio and extend the high resolution limit. Initial models were generated through rigid body refinement of a previously reported RPE65 crystal structure (PDB accession code 4RYY) using the program REFMAC. Ligand and water atoms were removed from the model prior to conducting the initial refinement. The model was then completed and optimized by multiple rounds of manual real space model building informed by MOLPROBITY close contact and geometry analyses in COOT followed by restrained reciprocal space refinement in REFMAC. Atomic coordinates and geometric restraint files for the ligands were generated with the Grade Web Server. Some bond angle restraint weights were manually adjusted to ensure ideal ligand stereochemistry. Residues 109-126 and 197-201 in the RPE65/MB-004 complex and 110-126, 197-201 and 267-271 in the RPE65/MB-008 complex were excluded from the final models owing to their poorly resolved electron densities. The soundness of the final models was assessed with the MOLPROBITY and wwPDB structure validation servers.

Results

Identification of Potential Sites for Emixustat Modification Based on RPE65 Crystal Structures The emixustat molecule can be divided into three basic regions: a polar aminopropanol moiety, a lipophilic methoxycyclohexyl ring and a central phenyl ring to which both the substituents are attached. MB-001 differs from emixustat in the substitution of a β-ionone ring in place of the cyclohexyl moiety. These molecules reside in the region of the RPE65 active site cavity that is proximal to its membrane embedded entrance. The aminopropanol moiety, located deepest within the binding pocket of the molecule, forms electrostatic interactions with Thr147, Glu148 as well as an iron-bound fatty acid carboxylate. Such interactions appear to contribute substantially to the binding affinity making alterations to this part of the molecule that disrupt active site binding affinity easily envisioned, for example removal or alkylation of the hydroxyl moiety. However, because such changes could influence the reactivity of the amino group towards retinal, we chose not to attempt modifications of this region of the molecule. Notably, we showed previously that emixustat forms a retinaldehyde Schiff base more efficiently than retinylamine, possibly as a consequence of the nearby hydroxyl moiety that can intramolecularly interact with the imine nitrogen atom.

The central phenyl ring is involved in π-π interactions with Phe103 as well as van der Waals contacts with a number of other active site residues. Notably, the active site region just above the phenyl ring is relatively polar with two well-ordered water molecules engaged in hydrogen bonding interactions with its constituent residues. These water molecules are located ~3.3 Å away from C5 of the emixustat molecule (FIG. 8A). We reasoned that introduction of a bulky lipophilic group to the region of the phenyl ring in close proximity to this polar pocket could effectively prevent binding of the derivative molecule to the RPE65 active site as a result of steric and electrostatic repulsive forces.

The terminal aliphatic ring moieties of these molecules, located closest to the active site entrance, are the most mobile regions of the molecule as evidenced by their higher average atomic displacement parameters (ADPs) and multiple conformations observed in different crystal forms. The long range van der Waals interactions formed between this portion of the molecules and residues forming the active site opening are expected to minimally contribute to the binding affinity of emixustat and MB-001. This region thus appeared to be a strong candidate for structure modification to improve active site binding affinity. Two binding cavities are present on either side of the cyclohexyl moiety, one polar and filled with water molecules and the other a small hydrophobic cavity formed by residues Ile259, Phe264, Tyr275, Cys278 and Phe279 that could serve as a site of interaction for suitable derivatives (FIG. 8B). In particular, we hypothesized that replacement of the terminal 6-membered ring with short linear moieties could result in molecules with the ability to engage these unexploited potential binding cavities.

To these ends, we developed novel synthetic routes for the generation of two classes of compounds; one series in which the terminal 6-membered ring of emixustat/MB-001 was substituted by either centrally coupled 4-heptyl-(MB-004) or 1-hydroxyhexan-3-yl (MB-008) groups and another in which an isopropyl moiety was added on the meta position of the phenyl ring with the terminal lipophilic moiety consisting of either cyclohexyl-(MB-005), 4-heptyl-(MB-006) or β-ionone (MB-007) groups (FIGS. 1A and B, left panels). Based on the structural features outlined above we hypothesized that the latter group of compounds would have severely impaired inhibitory activity towards RPE65 whereas the inhibitory activity of the former group could be enhanced owing to potential reinforced binding interactions. Both sets of compounds contained unmodified primary amine functionalities and were thus anticipated to retain retinaldehyde sequestration activity.

Figure 1B:
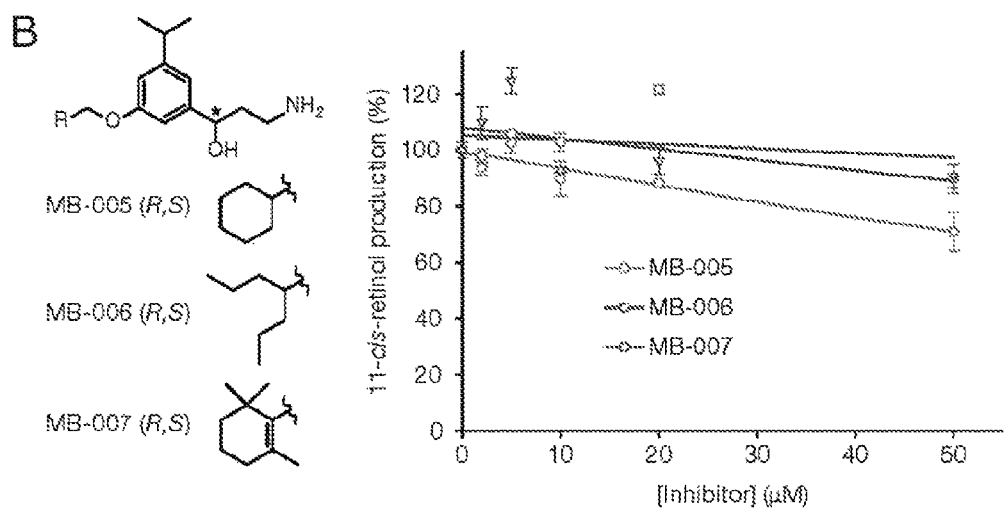

Changes to the Emixustat/MB-001 Core Structure Effectively Alter In Vitro Retinoid Isomerase Inhibitory Activity To test these structural predictions, we examined the inhibitory activity of the compounds against RPE65 activity in an in vitro retinoid isomerase assay using bovine RPE microsomes as the enzyme source. Consistent with our hypothesis, both MB-004 and MB-008 exerted more potent RPE65 inhibitory effects relative to emixustat and MB-001. Compared to emixustat, which is about 1.7 times more potent than MB-001, the two compounds MB-004 and MB-008 were approximately 2.2 and 1.2 times more potent with $IC_{50}$ values of 106±16 nM and 189±31 nM, respectively (FIG. 1A). Because the racemic forms of emixustat and MB-008 were used in these experiments, whereas MB-004 was synthesized as the pure R isomer, stereochemical differences must be accounted for when comparing the potencies of these compounds. We previously reported that R-emixustat is ~1.6 times more potent than the S-isomer. The estimated $IC_{50}$ of R-emixustat in this assay is therefore around 175 nM, making MB-004 approximately 1.7 times more potent in this head to head comparison. The four possible isomeric forms of MB-008 make head to head potency comparisons to emixustat more difficult, but the racemic mixture is at least as potent as R-emixustat and the possibility remains that one particular isomer could have even higher potency. Conversely, MB-005, MB-006 and MB-007 all exhibited minimal or no inhibition against retinoid isomerization in this assay up to concentrations of 50 μM, consistent with their inability to access the RPE65 active site and block retinyl ester uptake (FIG. 1B) Thus, these structure-guided modifications to the emixustat molecule modulated RPE65 inhibitory in a manner consistent with our expectations.

MB-004 AND MB-008 Engage Binding Sites in the RPE65 Active Site Cavity that are not Used by Emixustat and MB-001

Figure 3A:
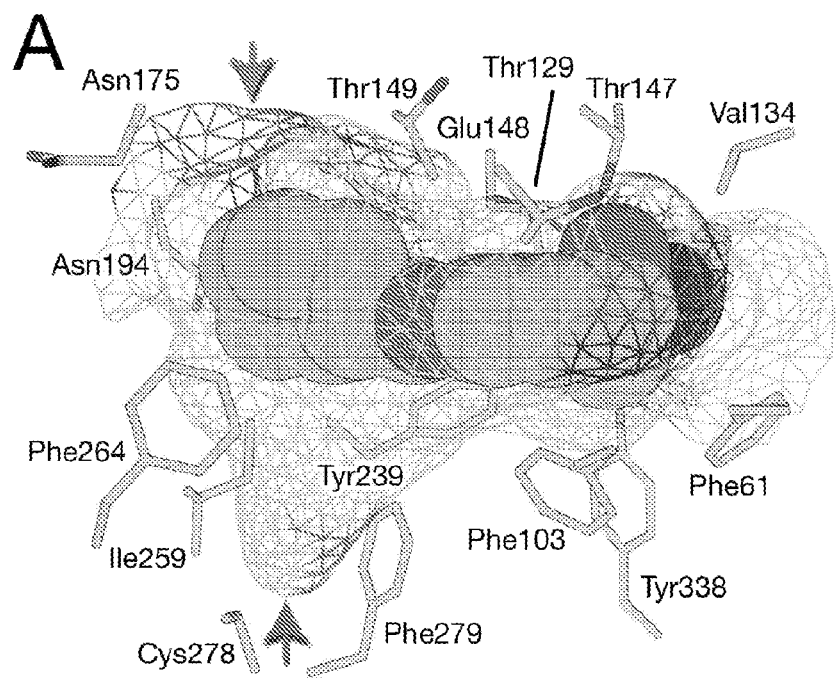
FIGS. 3(A-C) illustrate occupancy of MB ligands in the membrane-proximal binding pockets of the RPE65 cavity. Ligands are shown as van der Waals spheres with carbon, nitrogen and oxygen atoms. (A) The cyclohexyl ring of emixustat resides close to a polar, water-filled pocket (arrow) within the membrane-proximal region of the active site pocket. The bulkiness of the cyclohexyl moiety prevents it from occupying a nearby apolar pocket (arrow) with the potential to promote ligand binding through hydrophobic and van der Waals forces. (B) One half of the MB-004 dipropyl moiety occupies the aforementioned hydrophobic cavity forming van der Waals contacts with residues lining the pocket with the other half occupying a less constrained position near the active site opening. (C) The binding pose for MB-008 is nearly identical to that of MB-004. Notably, the polar hydroxyl tail of MB-008 fails to form significant hydrogen bonding or dipolar interactions with residues or water molecules making up the polar side of the proximal active site pocket.

To test our hypothesis that binding of MB-004 and MB-008 to the RPE65 active site could be strengthened by interactions with cavities located near the cyclohexanyl ring of emixustat, we determined crystal structures of native bovine RPE65 in complex with both molecules. The RPE65-MB-004 and RPE65-MB-008 structures, refined against data extending to 2.2 and 2.1 Å resolution, respectively, were obtained by co-crystallization with the compounds present in an approximately 5-fold molar excess over the protein under conditions similar to those used in prior RPE65-emixustat structure determinations (Table 1). In both cases, the ligands were clearly identified from the initial residual electron density maps (FIGS. 2A and B). The 3-amino-1-phenylpropan-1-ol moieties, common to MB-004, MB-008 and emixustat, were found in essentially identical conformations in all structures (FIG. 3). The (R)-isomer of the 3-amino-1-hydroxypropylphenyl moiety of MB-008 appeared to be the dominant form of the molecule occupying the active site, in agreement with our previous study on the binding of emixustat isomers to the RPE65 active site.

TABLE 1

| Data collection and processing[1] | | | |
|---|---|---|---|
| Crystal | MB-004[2] | MB-008 form 1 | MB-008 form 2[2] |
| X-ray source | NECAT-24 ID-E | NECAT-24 ID-E | NECAT-24 ID-C |
| Wavelength (Å) | 0.97919 | 0.97918 | 0.97920 |
| Unit cell parameters (Å) | a = 175.73, c = 86.37 | a = 175.32, c = 86.65 | a = 177.80, c = 86.23 |
| Space group | P6$_5$ | P6$_5$ | P6$_5$22 |
| Resolution (Å) | 50-2.20 (2.26-2.20) | 50-2.10 (2.23-2.10) | 50-2.25 (2.31-2.25) |
| Unique reflections | 77111 (5637) | 86966 (14111) | 38484 (2769) |
| Multiplicity | 12.1 (10.8) | 4.0 (3.9) | 21.2 (19.7) |
| Completeness (%) | 100 (100) | 98 (99) | 99.9 (99.2) |
| <I/σI> | 11.3 (1.2) | 9.34 (0.96) | 14.1 (1.0) |
| $R_{meas}$I (%) | 20.9 (228.1) | 15.2 (180.8) | 16.7 (341.2) |
| $CC_{1/2}$ (%) | 99.7 (40.1) | 99.6 (36.5) | 99.9 (45.7) |
| Refinement[3] | | | |
| Resolution (Å) | 47.9-2.2 | 47.9-2.1 | 48.2-2.25 |
| No reflections | 73171 | 82511 | 36613 |
| $R_{work}/R_{free}$ (%) | 17.0/20.9 | 17.6/21.1 | 17.0/20.7 |
| No atoms | 8894 | 8829 | 4273 |
| Protein | 8332 | 8187 | 4079 |
| Active site ligand/ions | Fe: 2 MB-004:40 Palmitate: 36 | Fe: 2 MB-008:40 Palmitate: 36 | Fe: 1 MB-008:20 Palmitate: 18 |
| Water | 447 | 530 | 141 |
| <B-factor> (Å$^2$) | 43.6 | 41 | 59.5 |
| Protein | 43.5 | 41 | 59.4 |
| Active site ligand/ions | Fe: 34 MB-004:41 Palmitate: 53 | Fe: 32 MB-008:44 Palmitate: 52 | Fe: 50.2 MB-008:74 Palmitate: 77 |
| Water | 44 | 43 | 57 |
| RMS deviations | | | |
| Bond lengths (Å) | 0.012 | 0.012 | 0.011 |
| Bond angles (°) | 1.55 | 1.54 | 1.55 |
| Ramachandran plot (% favored/outliers)[4] | 97.4/0 | 98.5/0 | 96.6/0 |
| Molprobity score (percentile) | 100$^{th}$ | 100$^{th}$ | 100$^{th}$ |

Figure 3B:
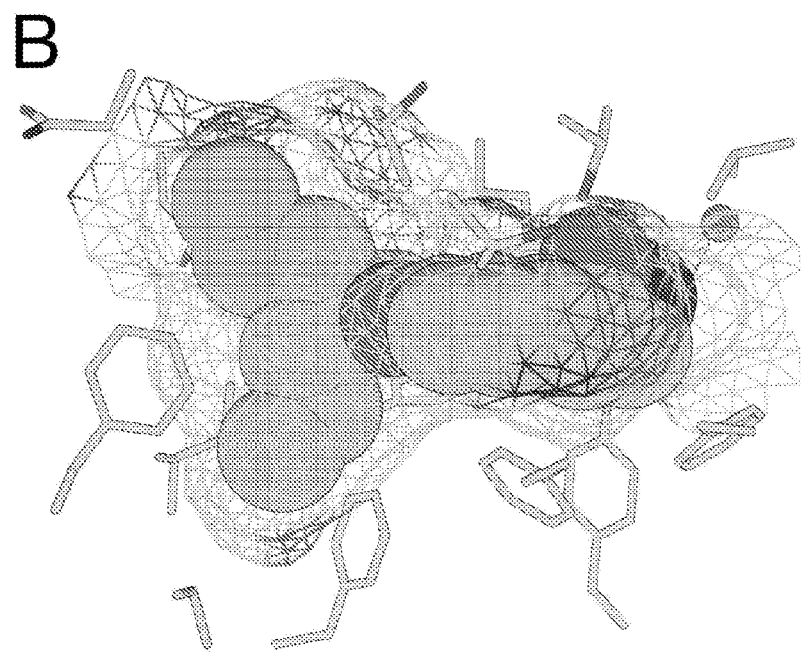
Figure 3C:
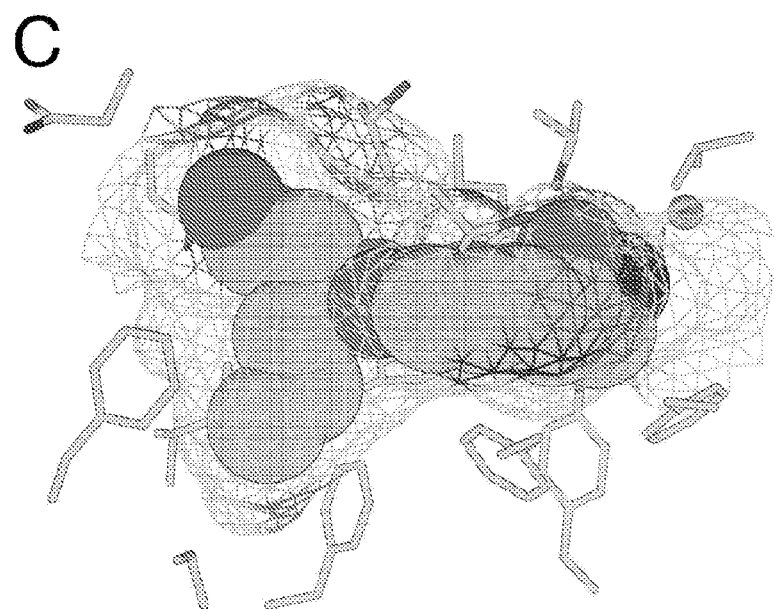

[1]Diffraction data processing was carried out using XDS
[2]Merged data from three crystals
[3]Structure refinement was carried out with REFMAC
[4]Assessed with Molprobity The dipropanyl tail of MB-004 adopted an extended conformation with one half of the moiety occupying the abovementioned hydrophobic cavity in van der Waals contact with the side chains of residues Ile259, Phe264, Tyr275 and Phe279 (FIG. 3B). The other half of this moiety chain was also found in an extended conformation near the active site tunnel entrance, but was less restrained, being held in place only by a few relatively less favorable van der Waals contacts with the Glu148 backbone carbonyl oxygen, backbone atoms of Gly176 and a nearby water molecule. This difference in binding interactions was reflected in the ~11% lower average B factor observed for the chain occupying the hydrophobic cavity (44 Å$^2$) compared to the other half of the substituent with sparser interaction partners (49 Å$^2$).

The 7-membered tail of MB-008 adopted a conformation very similar to that of MB-004 with the exception of a slight rotation of the hydroxyethyl moiety that allowed formation of a hydrogen bond with a water molecule located in the polar cavity mentioned above (FIG. 3C). This subtle difference in conformation was also observed in a separate RPE65-MB-008 crystal form (Table 1) suggesting that it represents a genuine structural difference. Trial refinements with the molecule modeled in the four possible isomers suggested that the S/R isomer of the molecule is the dominant form bound in the active site. Despite the apparently more favorable interaction made by the hydroxyethyl side chain its B-factors remained elevated compared to the rest of the molecule, similar to the analogous region of MB-004.

In summary, the replacement of the emixustat cyclohexanyl tail with a short linear alkane moiety appeared to strengthen binding affinity owing to the fulfillment of favorable van der Waals and hydrophobic interactions with a lipophilic pocket located near the active site entrance. The presence of a second linear moiety with a capacity to form hydrogen bonding interactions with polar residues and solvent molecules located across from the lipophilic pocket appeared to contribute minimally to the binding affinity of MB-008.

Effects of MB Compounds on In Vivo Visual Cycle Function

Figure 4:
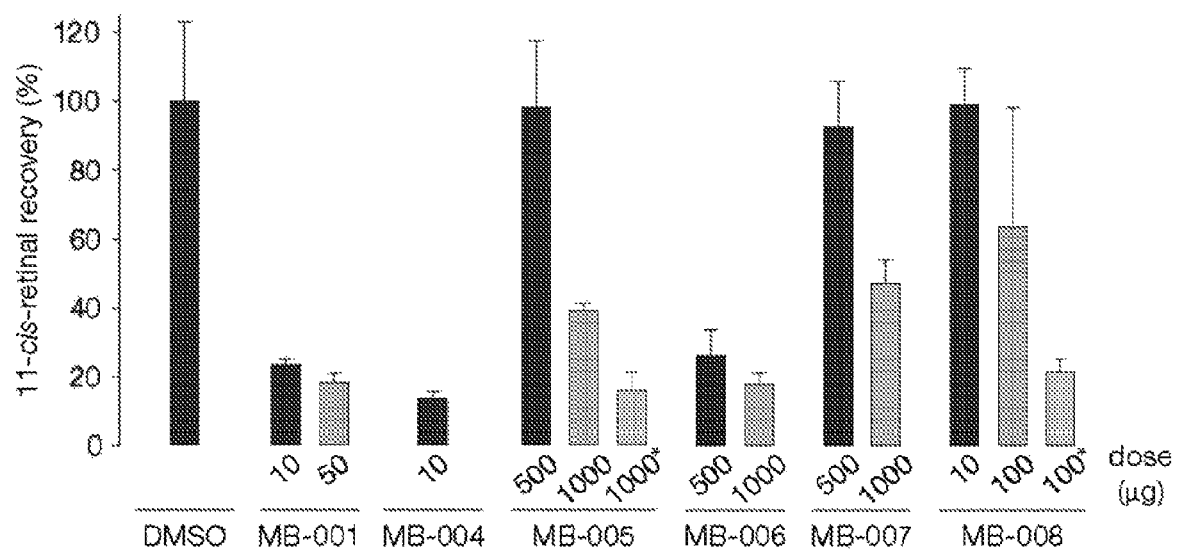
FIG. 4 illustrates inhibition of visual chromophore regeneration in C57BL6J mouse eyes by MB compounds. The MB drugs were administrated to mice by oral gavage 24 h prior to light exposure for 10 min. Then all mice recovered under darkness for 6 h. The 11-cis-retinal ocular levels were measured with HPLC, and all the values are expressed as percentages of the control group (displayed as means±SD; n=3 for each group except the MB-008 group in which n=9).

Next, we tested the effects of the MB compound series on retinoid cycle function in the living mouse. For these experiments, mice were administered a single dose of the test compound by oral gavage and 24 h later they were subjected to light exposure that resulted in 95% of rhodopsin being bleached. After the light treatment, mice were allowed to dark adapt for 6 h before their ocular retinoid content was determined by HPLC. MB-004, at a dose of 10 μg/mouse dramatically suppressed visual chromophore regeneration to at least the same degree as MB-001 at the same dose (FIG. 4). By contrast, mice treated with 10 μg of MB-008 recovered visual chromophore to a level comparable to vehicle-treated mice with a ten-fold higher dose resulting in only a 30% suppression in visual cycle function, which was unexpected given the strong in vitro retinoid isomerase inhibitory effects of this compound (FIG. 1A). To examine the possibility that the lack of MB-008 efficacy at 24 h was due to insufficient concentrations resulting from a shorter elimination half-life or poorer bioavailability, we repeated the experiment with the mice subjected to light exposure 4 h after MB-008 administration. A 100 μg dose of MB-008 suppressed visual chromophore regeneration by ~80%, supporting the idea that the retinal concentration of MB-008 could be sub-effective at the longer post-treatment light challenge.

Despite the near absence of in vitro retinoid isomerase inhibitory effects for MB-005, MB-006 and MB-007 (FIG. 1B), these compounds were able to discernably slow chromophore regeneration in the living mouse albeit at doses much higher than those used for MB-001 (FIG. 4). Five-hundred g doses of MB-005 and MB-007 had minimal effects on 11-cis-retinal recovery, whereas ~50% inhibition was observed with both compounds at a two-fold higher dose. By contrast, 500 and 1000 μg of MB-006 suppressed visual chromophore production to ~30% and ~20% of the vehicle control, respectively. Similar to MB-008, we found in the case of MB-005 that shortening the time between drug administration and the light challenge enhanced the inhibitory effects of the treatment suggesting that substantial MB-005 clearance occurs in the 24 h following drug administration.

Impact of Visual Cycle Modulators on the Mouse ERG

Figure 5:
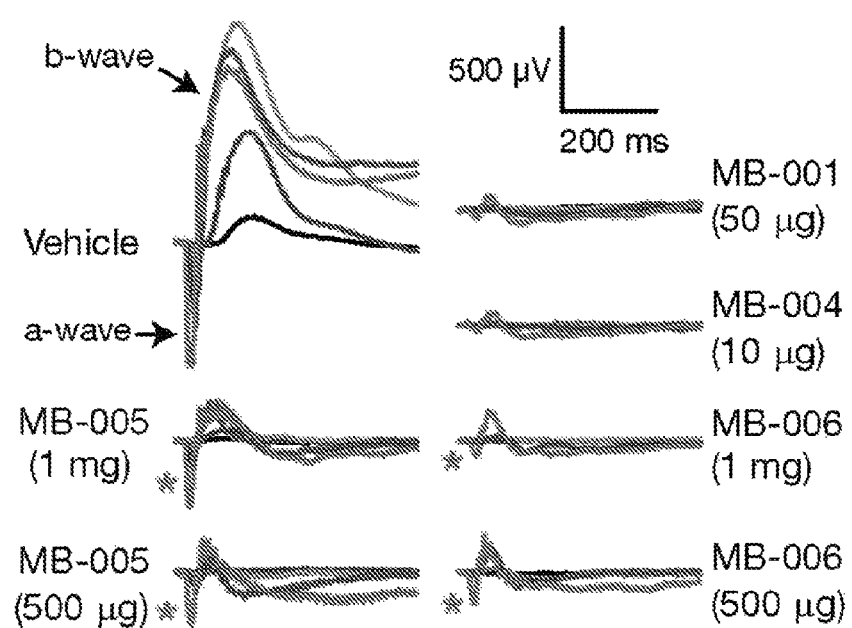
FIG. 5 illustrates ERG responses of mice treated with visual cycle modulators. Oral gavage was used to administer vehicle or MB compounds to mice 24 h prior to 10 min light exposure followed by 6 h of dark adaptation. Dark-adapted ERGs were obtained to strobe flash stimuli.

We next examined the impact of these compounds on retinal function, measured using the electroretinogram (ERG). FIG. 5 presents a family of dark-adapted ERGs measured 6 hours after mice underwent a 95% bleach presented 1 day following gavage administration of vehicle or MB compound molecules at doses indicated to be effective by retinoid analysis. Mice gavaged with vehicle (Veh) alone had ERGs that were comparable to those obtained in a pre-treatment baseline study. In comparison, mice administered with MB compound molecules had had reduced amplitude ERGs indicative of incomplete bleaching recovery. For example, mice treated with MB-001 and MB-004 had responses to low luminance stimuli that were not different from background noise levels. In response to higher luminance stimuli, reproducible responses were observed. That these reflect dark-adapted cone-mediated responses is supported by their similarity to responses obtained from transducin KO mice which lack rod-mediated activity, while retaining normal cone-mediated responses, and have a very similar ERG phenotype. Mice treated with MB-005 and MB-006 had less incomplete recovery, as evidenced by a small amplitude electronegative a-wave to high luminance stimuli.

Isopropyl Emixustat Derivatives Distribute into the Eye and Form Retinal Schiff Base Conjugates In Vivo The unexpected ability of the isopropyl emixustat derivatives to slow visual chromophore regeneration indicated that the ocular distribution of these compounds was preserved in spite of the structural modification. To confirm the ocular distribution of this compound series, we directly measured the quantity of MB-005 in the eye by mass spectrometry after a 1 mg dose. Using emixustat as an internal standard we determined that the ocular level of MB-005 attained 6 h after treatment was ~140 ng/eye and declined only slightly at the 24 h post-treatment time point. This minimal change in ocular MB-005 concentration contrasts with the ~3-fold greater inhibition of visual cycle function observed at 4 h versus 24 h for this compound. These results indicate that the isopropyl-derivative series compounds could persist in the eye for extended periods of time to exert their effects.

Figure 6A:
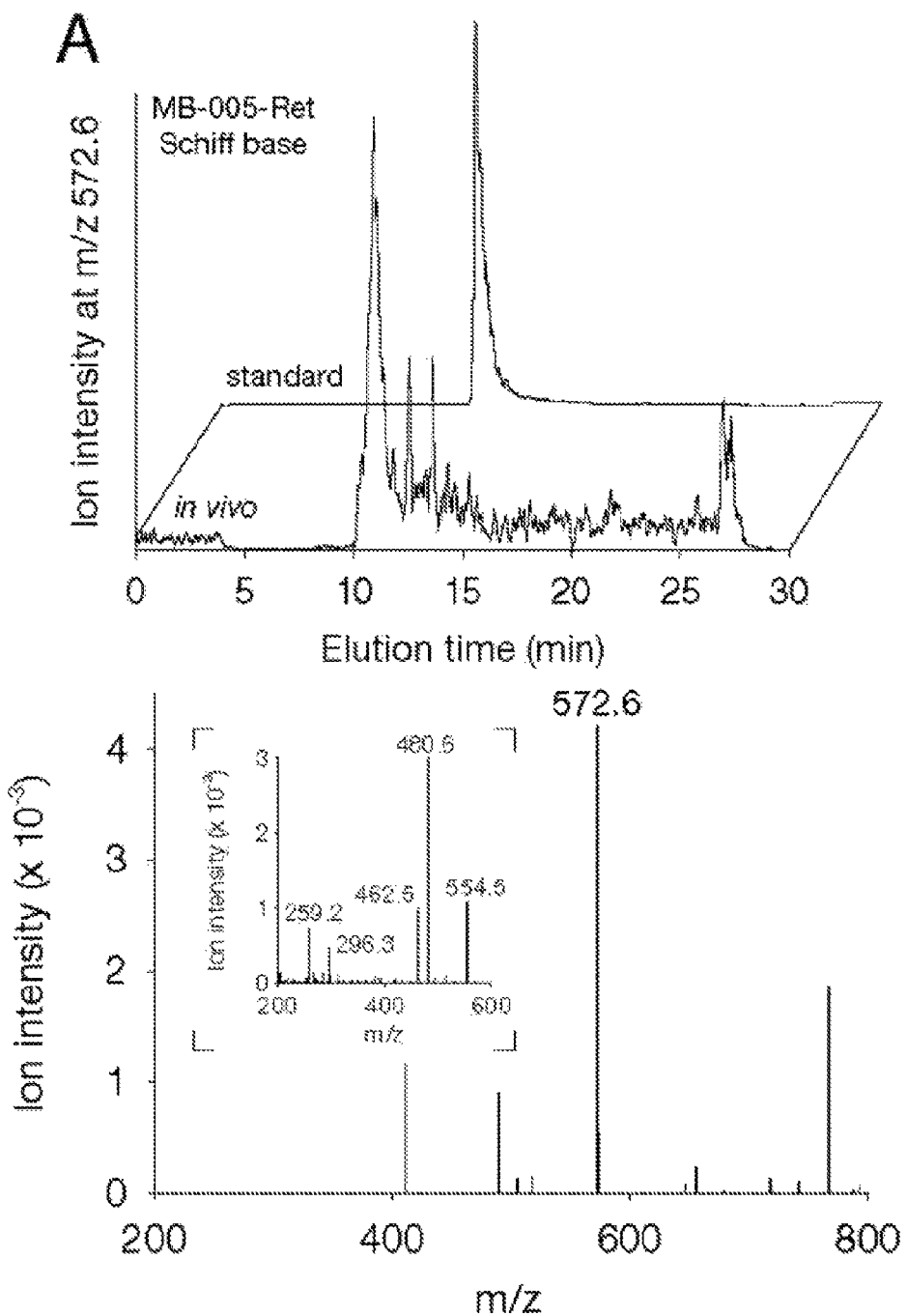
FIGS. 6(A-B) illustrate identification of retinal Schiff base conjugates in $Abca4^{-/-}$ $Rdh8^{-/-}$ mice treated with MB-005 and MB-006. Following drug administration, mice were exposed to intense light for 10 min. After a 30 min recovery under darkness, animals were sacrificed and retinoids were extracted from the eyes. (A, B) Shown in the top panels are selective ion chromatograms for MB-005-retinal conjugates (A, at m/z=572.6) and MB-006-retinal conjugates (B, at m/z=588.6). Panels on the bottom show the mass spectra of the peaks coinciding with the retention times of their authentic standards. The insets display the MS/MS fragmentation patterns of the two imines, which were identical to the corresponding standards.
Figure 6B:
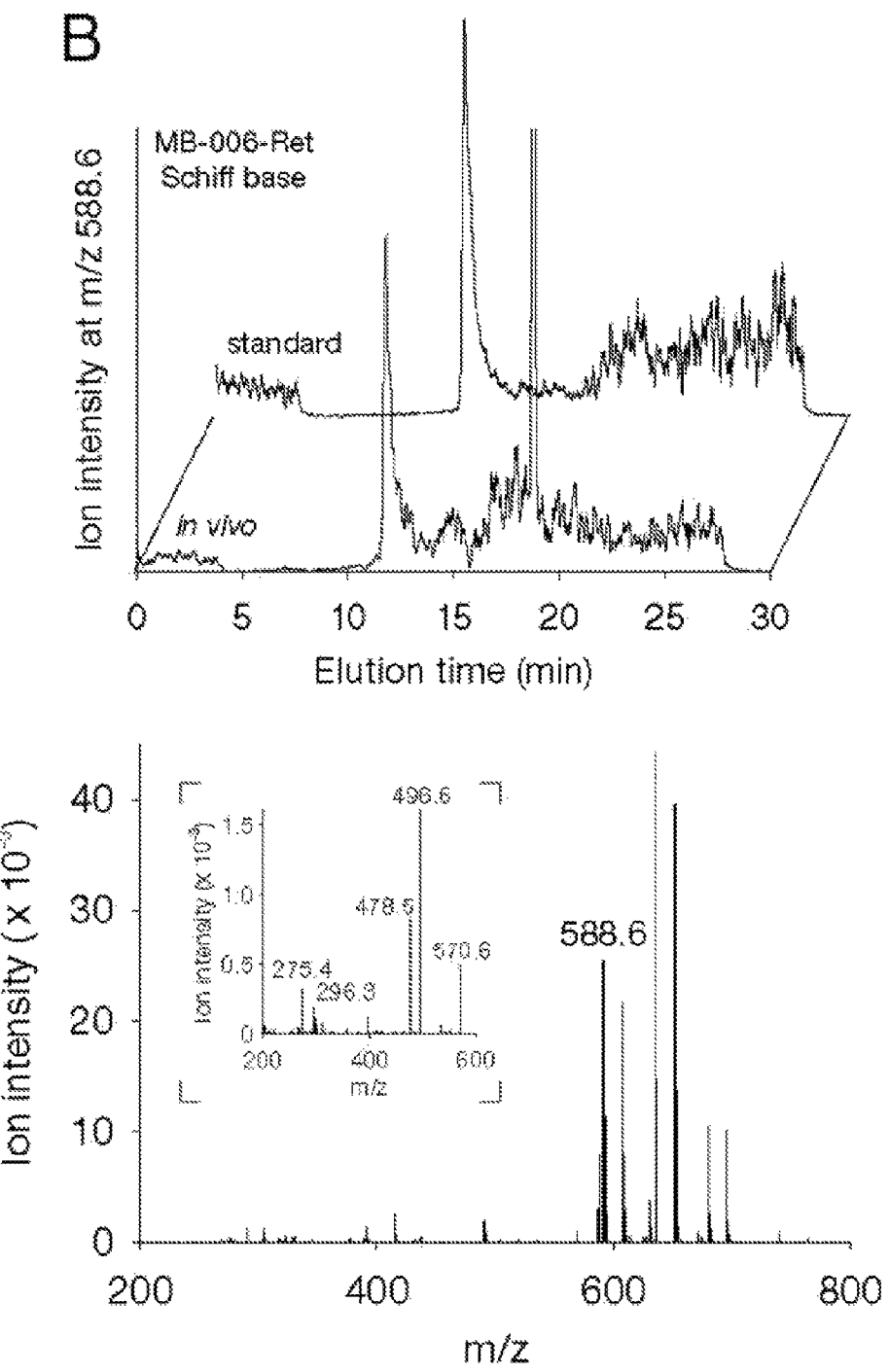

With the effects of these compounds on visual cycle function established we next sought to examine their ability to form retinal-Schiff base conjugates in vivo. For these experiments Abca4$^{-/-}$Rdh8$^{-/-}$ mice, a model for Stargardt macular dystrophy that exhibits delayed all-trans-retinal clearance, were administered MB-005 or MB-006 and then 6 h later subjected to bright light exposure. Retinoids were extracted and analyzed by mass spectrometry. MB-005- and MB-006-retinal Schiff base adducts formed in vitro were prepared for use as standards. Acetonitrile extracts from the eyes of mice treated with either MB-005 or MB-006 both contained compounds matching the expected molecular weight of the respective Schiff base adducts with retention times (FIGS. 6A and B, left) and tandem mass spectra (FIGS. 6A and B, right) exactly matching those of the standards. These data demonstrate that emixustat derivatives with substitutions that alter their ability to directly inhibit RPE65 have a preserved ability to form retinaldehyde Schiff base adducts in vivo suggesting that they can exert protective effects against retinaldehyde toxicity.

Protective Effects of MB Compounds Against Retinal Phototoxicity

To examine the ability of the MB compounds to protect against retinal phototoxicity we administered the compounds to Abca4$^{-/-}$Rdh8$^{-/-}$ mice by oral gavage and after 24 h exposed the mice to white light of sufficient intensity to cause retinal damage in the absence of treatment with protective agents. Three days later retinas were imaged in vivo by optical coherence tomography, with preservation of outer nuclear layer thickness and light scattering properties serving as markers for retinal health. MB-001, which is capable of preventing light-induced retinal degeneration through both direct RPE65 inhibition as well as retinal sequestration served as a positive control for these experiments.

MB-004 at a dose about 2.5 times greater than that required for near complete suppression of in vivo visual cycle function (25 μg) resulted in an approximately 80% protective effect relative to MB-001, which was fully protective at a dose of 50 μg (FIG. 7). This data showing incomplete retinal protection in the face of profound visual cycle suppression suggested an incomplete causal relationship between the two activities. In other words, the lack of full outer nuclear layer preservation observed for MB-004 supports the idea that retinal protection exerted by retinal sequestering compounds is not fully explained by their degree of visual cycle inhibition. MB-008, which also directly inhibits RPE65, was poorly protective even at doses as high as 0.25 mg when administered 24 h prior to the light challenge. Consistent with our in vivo visual chromophore regeneration assay suggesting that MB-008 concentrations are lower compared to MB-004, we found that shortening the duration between compound administration and the light challenge from 24 to 6 h substantially improved the protective effects of the compound. However, even after these shorter time periods, MB-008 could only exert full protection at a dose ten-times higher than that used for MB-004, which would be expected to near maximally suppress visual cycle function.

The isopropyl MB compound series also exerted variable protective effects (FIG. 7). At one extreme, MB-007 was no more protective than vehicle control even at a dose of 1 mg per mouse, even though this compound unexpectedly suppressed visual chromophore regeneration by ~50% at the same dose (FIG. 4). MB-006 was protective at a dose of 1 mg but not 0.5 mg per mouse. Like MB-007, the 0.5 mg dose of MB-006 strongly suppressed visual cycle function suggesting that such inhibition is irrelevant to the retinal protective effects of these compounds (FIG. 4). MB-005 was unique amongst this set of compounds in its ability to confer protection against retinal phototoxicity at doses that preserved substantial visual cycle function. At a dose of 0.5 mg/mouse, which had no measurable effect on visual cycle function (FIG. 4), MB-005 treatment resulted in an ~50% protective effect compared to the MB-001 control (FIG. 7). Doubling the dose resulted in an ~80% protective effect, similar to a 25 μg dose of MB-004 (FIG. 7), with approximately 60% suppression of visual chromophore regeneration activity (FIG. 4). A 2 mg/mouse dose of MB-005 fully protected the retina from light damage although visual cycle function was also severely impaired at this dose (FIGS. 4 and 7).

Taken together these data demonstrate that the ability of primary amine emixustat-like molecules to protect against light-induced retinal degeneration is poorly correlated with their ability to slow visual cycle activity.

We found that molecules capable of occupying a hydrophobic pocket near the active site opening, namely MB-004 and MB-008, exhibit superior in vitro RPE65 inhibitory activity relative to emixustat and MB-001, whereas the presence of a polar moiety in the case MB-008 did not appear to substantially contribute to binding affinity. It is likely that binding affinity could be further improved through careful consideration of the binding pocket volume and geometry.

It has previously been shown in the case of hydrophobic pockets that moieties occupying ~55% of the available binding space tend to be optimal in terms of binding affinity. The RPE65 hydrophobic pocket discussed here has a volume of approximately 154 Å$^3$ whereas the volume of a propyl group is ~63 Å$^3$, suggesting that expansion of the alkyl chain length by one methylene group, which would result in a molecular volume of ~79 Å$^3$, could further improve binding affinity.

Likewise, the binding strength of ordered waters within the hydrophilic cavity could inform strategies for maximizing ligand interactions at this site. Weakly bound water molecules, which typically engage in three or fewer hydrogen bonding interactions with the protein, can be targeted for displacement by appropriately positioned polar ligand substituents as release of the water molecule in this situation is expected to be thermodynamically favorable. Conversely, there can be a substantial energetic cost to displacing more strongly bound waters and it these cases it is likely better if the ligand is designed to favorably interact, rather than displace, the ordered water molecule. Waters contained within the RPE65 hydrophilic pocket are all engaged in three or more hydrogen bonding interactions, two of which are formed with protein atoms and the remainder with adjacent water molecules. The binding strength of these waters will likely require detailed calculations to be accurately estimated. However, the hydroxyl group of MB-008 was clearly incapable of accomplishing the displacement, instead forming a relatively weak additional hydrogen bond with one of the resident water molecules. Suitable polar modifications can be expected to strengthen ligand binding. However, any potential gains in binding affinity could be offset by poorer membrane permeability, which could compromise bioavailability and distribution to the site of action in the RPE.

High affinity RPE65 inhibitors could find potential use both in the clinic as well as in the lab. Highly selective RPE65 inhibitors could be important tools for elucidating the role of RPE65 in the visual function of animals with cone-dominated retinas. Cones are thought to receive their visual chromophore from both the classical visual cycle as well as an intraretinal, Muller-cell based pathway that allow for sustain regeneration under high illumination conditions. The relative contribution of RPE65 to cone cell function remains unclear. Highly potent and selective RPE65 inhibitors could be employed to eliminate classical visual cycle function in cone dominant species such as the ground squirrel. Such conditions would allow for detailed examination of the intraretinal visual cycle in isolation.

In patients with Stargardt disease in which A2E is thought to be a primary contributor to macular degeneration, direct RPE65 inhibition by emixustat-like molecules can be therapeutically advantageous as it was previously reported that emixustat and its predecessor retinylamine lower A2E formation in mouse models of Stargardt disease. Additionally, these compounds also exert beneficial effects in mouse models of diabetic retinopathy that are thought to be directly related to their ability to inhibit RPE65. Improving the visual cycle modulator potency could lessen any off target side effects. However, clinical trials with emixustat indicate that side effects directly related to RPE65 inhibition including night blindness and dyschromatopsia are most problematic for patients. Tighter binding inhibitors could have prolonged effects that are less well tolerated. A molecule with a shorter duration of action, like that of MB-008, could be advantageous for lessening the adverse effects associated with visual cycle suppression.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A method of decreasing all-trans retinal accumulation in ocular tissue in a subject in need thereof, the method comprising:
   administering to the subject a therapeutically effective amount of a retinal sequestering compound of formula (II):

$$(II)$$

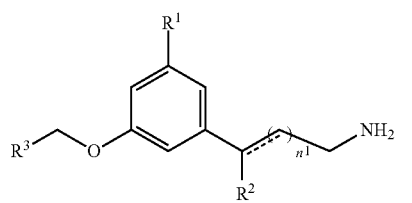

wherein $n^1$ is an integer from 1 to 6;
$R^1$ is selected from the group consisting of:

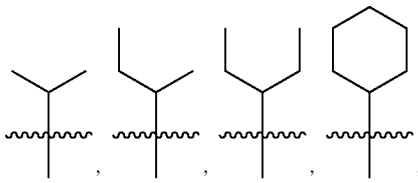

and fluoro derivatives thereof;
$R^2$ is H, $CH_3$, or OH;
$R^3$ is a substituted or unsubstituted $C_1$-$C_{12}$ alkyl, $C_2$-$C_{12}$ alkenyl, $C_2$-$C_{12}$ alkynyl, $C_3$-$C_6$ aryl, heteroaryl, heterocyclyl, or $C_6$-$C_{12}$ alkaryl;
the dashed line is an optional bond; and
deuterated compounds and pharmaceutically acceptable salts thereof.

2. The method of claim 1, wherein $R^1$ does not include acidic or basic functional groups.

3. The method of claim 1, wherein $R^1$ is a branched or cyclic $C_3$-$C_{24}$ alkyl or fluoroalkyl.

4. The method of claim 1, wherein $R^3$ is selected from the group consisting of:

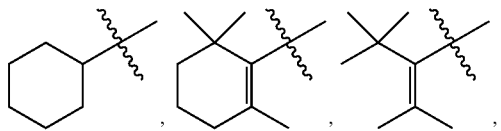

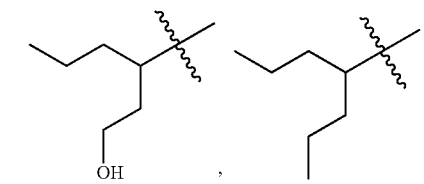

and fluoro derivatives thereof.

5. The method of claim 1, the retinal sequestering compound upon administration to the subject transiently sequestering all-trans-retinal in ocular tissue of a subject by forming a reversible Schiff-base with the all-trans-retinal, wherein the retinal sequestering compound does not adversely affect normal retinoid cycle performance.

* * * * *